United States Patent
Ogdahl et al.

(10) Patent No.: US 9,144,426 B2
(45) Date of Patent: Sep. 29, 2015

(54) SURGICAL ARTICLES AND METHODS FOR TREATING PELVIC CONDITIONS

(75) Inventors: Jason W. Ogdahl, Minnetonka, MN (US); Jessica L. Roll, Minnetonka, MN (US); Mona N. Dahdah, Minnetonka, MN (US); Robert E. Lund, Minnetonka, MN (US); John F. Otte, Minnetonka, MN (US); Karen Pilney Montpetit, Minnetonka, MN (US); Chaouki A. Khamis, Minnetonka, MN (US); Richard C. Kaleta, Minnetonka, MN (US); Kelly Ann Chapman, Minnetonka, MN (US); Jelica D. Wold, Minnetonka, MN (US)

(73) Assignee: AMS Research Corporation, Minnetonka, MN (US)

( * ) Notice: Subject to any disclaimer, the term of this patent is extended or adjusted under 35 U.S.C. 154(b) by 1755 days.

(21) Appl. No.: 12/223,846

(22) PCT Filed: Feb. 16, 2007

(86) PCT No.: PCT/US2007/004015
§ 371 (c)(1), (2), (4) Date: Jun. 7, 2010

(87) PCT Pub. No.: WO2007/097994
PCT Pub. Date: Aug. 30, 2007

(65) Prior Publication Data
US 2010/0256442 A1  Oct. 7, 2010

Related U.S. Application Data

(60) Provisional application No. 60/775,039, filed on Feb. 16, 2006, provisional application No. 60/804,353, filed on Jun. 9, 2006, provisional application No. 60/805,040, filed on Jun. 16, 2006, provisional application No. 60/806,073, filed on Jun. 28, 2006.

(51) Int. Cl.
*A61F 2/02* (2006.01)
*A61F 2/00* (2006.01)
(Continued)

(52) U.S. Cl.
CPC ......... *A61B 17/06109* (2013.01); *A61F 2/0045* (2013.01); *A61B 17/0401* (2013.01);
(Continued)

(58) Field of Classification Search
CPC ..... A61F 2/0045; A61F 2/005; A61F 2/0036; A61F 2/0063; A61F 5/48; A61B 2017/00805; A61B 17/0401; A61B 17/06109
USPC ......... 600/29–32, 37; 128/834, 885, 897–899
See application file for complete search history.

(56) References Cited

U.S. PATENT DOCUMENTS 4,548,202 A   10/1985  Duncan
5,112,344 A   5/1992   Petros
(Continued)

FOREIGN PATENT DOCUMENTS

DE   19544162    4/1997
DE   10211360    10/2003
(Continued)

OTHER PUBLICATIONS

Stamey, T.A., "Endoscopic Suspension of the Vesical Neck for Urinary Incontinence in Females," Ann. Surg., pp. 465-471, Oct. 1980.
(Continued)

*Primary Examiner* — Christine H Matthews
*Assistant Examiner* — Sunita Reddy
(74) *Attorney, Agent, or Firm* — Kagan Binder, PLLC

(57) ABSTRACT

A pelvic implant assembly (100) comprising a support portion (128) and an extension portion (124), a self-fixating tip (10, 120) connected to the extension portion, the self-fixating tip comprising a base (12) comprising a proximal base end (14) and a distal base end (16), the proximal base end being connected to the extension portion, the base comprising an internal channel (18) extending from the proximal base end and at least partially along a length of the base toward the distal base end, a fixed lateral extension (20) extending from the base.

28 Claims, 21 Drawing Sheets

(51) Int. Cl.
*A61B 17/06* (2006.01)
*A61B 17/04* (2006.01)
*A61B 17/00* (2006.01)

(52) U.S. Cl.
CPC ............ *A61B2017/00805* (2013.01); *A61B 2017/0412* (2013.01); *A61B 2017/0424* (2013.01); *A61B 2017/0427* (2013.01); *A61B 2017/0437* (2013.01); *A61B 2017/0445* (2013.01); *A61B 2017/0454* (2013.01); *A61B 2017/0458* (2013.01); *A61B 2017/0464* (2013.01); *A61B 2017/06042* (2013.01); *A61B 2017/06176* (2013.01)

(56) References Cited

U.S. PATENT DOCUMENTS

| | | | |
|---|---|---|---|
| 5,256,133 | A | 10/1993 | Spitz |
| 5,269,783 | A | 12/1993 | Sander |
| 5,362,294 | A | 11/1994 | Seitzinger |
| 5,591,206 | A | 1/1997 | Moufarrege |
| 5,611,515 | A | 3/1997 | Benderev et al. |
| 5,669,935 | A | 9/1997 | Rosenman et al. |
| 5,842,478 | A | 12/1998 | Benderev et al. |
| 5,860,425 | A | 1/1999 | Benderev et al. |
| 5,899,909 | A | 5/1999 | Claren et al. |
| 5,954,057 | A | 9/1999 | Li |
| 6,039,686 | A | 3/2000 | Kovac |
| 6,042,534 | A | 3/2000 | Gellman et al. |
| 6,042,536 | A | 3/2000 | Tihon et al. |
| 6,110,101 | A | 8/2000 | Tihon et al. |
| 6,200,330 | B1 | 3/2001 | Benderev et al. |
| 6,328,744 | B1 | 12/2001 | Harari et al. |
| 6,382,214 | B1 | 5/2002 | Raz et al. |
| 6,451,024 | B1 | 9/2002 | Thompson et al. |
| 6,506,190 | B1 | 1/2003 | Walshe |
| 6,592,515 | B2 | 7/2003 | Thierfelder et al. |
| 6,592,610 | B2 | 7/2003 | Beyar |
| 6,612,977 | B2 | 9/2003 | Staskin et al. |
| 6,638,211 | B2 | 10/2003 | Suslian et al. |
| 6,641,524 | B2 | 11/2003 | Kovac |
| 6,641,525 | B2 | 11/2003 | Rocheleau et al. |
| 6,652,450 | B2 | 11/2003 | Neisz et al. |
| 6,673,010 | B2 | 1/2004 | Skiba et al. |
| 6,685,629 | B2 | 2/2004 | Therin |
| 6,691,711 | B2 | 2/2004 | Raz et al. |
| 6,830,052 | B2 | 12/2004 | Carter et al. |
| 6,881,184 | B2 | 4/2005 | Zappala |
| 6,908,473 | B2 | 6/2005 | Skiba et al. |
| 6,911,002 | B2 | 6/2005 | Fierro |
| 6,911,003 | B2 | 6/2005 | Anderson et al. |
| 6,960,160 | B2 | 11/2005 | Browning |
| 6,974,462 | B2 | 12/2005 | Sater |
| 6,981,983 | B1 | 1/2006 | Rosenblatt et al. |
| 7,014,607 | B2 | 3/2006 | Gellman |
| 7,048,682 | B2 | 5/2006 | Neisz et al. |
| 7,056,333 | B2 | 6/2006 | Walshe |
| 7,070,556 | B2 | 7/2006 | Anderson et al. |
| 7,083,568 | B2 | 8/2006 | Neisz et al. |
| 7,112,210 | B2 | 9/2006 | Ulmsten et al. |
| 7,131,943 | B2 | 11/2006 | Kammerer |
| 7,131,944 | B2 | 11/2006 | Jacquetin |
| 7,175,591 | B2 | 2/2007 | Kaladelfos |
| 7,229,404 | B2 | 6/2007 | Bouffier |
| 7,297,102 | B2 | 11/2007 | Smith et al. |
| 7,326,213 | B2 | 2/2008 | Benderev et al. |
| 7,351,197 | B2 | 4/2008 | Montpetit et al. |
| 7,364,541 | B2 | 4/2008 | Chu et al. |
| 7,371,245 | B2 | 5/2008 | Evans et al. |
| 7,387,634 | B2 | 6/2008 | Benderev |
| 7,393,320 | B2 | 7/2008 | Montpetit et al. |
| 7,407,480 | B2 | 8/2008 | Staskin et al. |
| 7,410,460 | B2 | 8/2008 | Benderev |
| 7,413,540 | B2 | 8/2008 | Gellman et al. |
| 7,422,557 | B2 | 9/2008 | Arnal et al. |

| | | | |
|---|---|---|---|
| 2002/0007222 | A1 | 1/2002 | Desai |
| 2002/0161382 | A1 | 10/2002 | Neisz et al. |
| 2003/0135225 | A1 | 7/2003 | Harari et al. |
| 2003/0176875 | A1 | 9/2003 | Anderson et al. |
| 2004/0006353 | A1 | 1/2004 | Bosley, Jr. et al. |
| 2004/0225181 | A1 | 11/2004 | Chu et al. |
| 2004/0230206 | A1 | 11/2004 | Gellman et al. |
| 2004/0249397 | A1 | 12/2004 | Delorme et al. |
| 2004/0267088 | A1 | 12/2004 | Kammerer |
| 2005/0000523 | A1 | 1/2005 | Beraud |
| 2005/0004427 | A1 | 1/2005 | Cervigni |
| 2005/0021086 | A1 | 1/2005 | De Leval |
| 2005/0038451 | A1 | 2/2005 | Rao et al. |
| 2005/0043580 | A1 | 2/2005 | Watschke et al. |
| 2005/0065395 | A1 | 3/2005 | Mellier |
| 2005/0131391 | A1 | 6/2005 | Chu et al. |
| 2005/0131393 | A1 | 6/2005 | Chu et al. |
| 2005/0199249 | A1 | 9/2005 | Karram |
| 2005/0245787 | A1 | 11/2005 | Cox et al. |
| 2005/0256530 | A1 | 11/2005 | Petros |
| 2005/0277806 | A1 | 12/2005 | Cristalli |
| 2005/0278037 | A1 | 12/2005 | Delorme et al. |
| 2005/0283189 | A1 | 12/2005 | Rosenblatt |
| 2006/0015005 | A1 | 1/2006 | Sater |
| 2006/0041185 | A1 | 2/2006 | Browning |
| 2006/0058575 | A1 | 3/2006 | Zaddem et al. |
| 2006/0058578 | A1 | 3/2006 | Browning |
| 2006/0089524 | A1 | 4/2006 | Chu |
| 2006/0089525 | A1 | 4/2006 | Mamo et al. |
| 2006/0122457 | A1 | 6/2006 | Kovac et al. |
| 2006/0173237 | A1 | 8/2006 | Jacquetin |
| 2006/0195007 | A1 | 8/2006 | Anderson et al. |
| 2006/0195010 | A1 | 8/2006 | Arnal et al. |
| 2006/0195011 | A1 | 8/2006 | Arnal et al. |
| 2006/0217589 | A1 | 9/2006 | Wan et al. |
| 2006/0229493 | A1* | 10/2006 | Weiser et al. ............ 600/37 |
| 2006/0229596 | A1 | 10/2006 | Weiser et al. |
| 2006/0235262 | A1 | 10/2006 | Arnal et al. |
| 2006/0252980 | A1 | 11/2006 | Arnal et al. |
| 2006/0260618 | A1 | 11/2006 | Hodroff et al. |
| 2006/0287571 | A1 | 12/2006 | Gozzi et al. |
| 2007/0015953 | A1 | 1/2007 | MacLean |
| 2007/0078295 | A1 | 4/2007 | Landgrebe |
| 2007/0123746 | A1 | 5/2007 | MacLean |
| 2007/0173864 | A1 | 7/2007 | Chu |
| 2008/0039678 | A1 | 2/2008 | Montpetit et al. |
| 2008/0300607 | A1 | 12/2008 | Meade et al. |
| 2009/0005634 | A1 | 1/2009 | Rane |
| 2009/0012353 | A1 | 1/2009 | Beyer |

FOREIGN PATENT DOCUMENTS

| | | |
|---|---|---|
| DE | 202006016866 | 3/2007 |
| EP | 0248544 | 9/1987 |
| EP | 0632999 | 1/1995 |
| EP | 1600118 | 11/2005 |
| EP | 1609439 | 12/2005 |
| EP | 1342450 | 1/2007 |
| FR | 2787990 | 7/2000 |
| FR | 2852813 | 10/2004 |
| GB | 2353220 | 2/2001 |
| WO | WO 99/59477 | 11/1999 |
| WO | WO 00/74594 | 12/2000 |
| WO | WO 00/74633 | 12/2000 |
| WO | WO 02/30293 | 4/2002 |
| WO | WO 02/38079 | 5/2002 |
| WO | WO 03/013392 | 2/2003 |
| WO | WO 03/075792 | 9/2003 |
| WO | WO 03/092546 | 11/2003 |
| WO | WO 03/096928 | 11/2003 |
| WO | WO 03/096929 | 11/2003 |
| WO | WO 2004/012626 | 2/2004 |
| WO | WO 2004/017862 | 3/2004 |
| WO | WO 2004/034912 | 4/2004 |
| WO | WO 2005/037132 | 4/2005 |
| WO | WO 2005/079702 | 9/2005 |
| WO | WO 2005/107606 | 11/2005 |
| WO | WO 2005/122954 | 12/2005 |
| WO | WO 2006/003314 | 1/2006 |

(56) References Cited

FOREIGN PATENT DOCUMENTS

| | | |
|---|---|---|
| WO | WO 2006/005117 | 1/2006 |
| WO | WO 2006/015031 | 2/2006 |
| WO | WO 2006/045042 | 4/2006 |
| WO | WO 2006/108145 | 10/2006 |
| WO | WO 2007/014241 | 2/2007 |
| WO | WO 2007/016083 | 2/2007 |
| WO | WO 2007/027592 | 3/2007 |
| WO | WO 2007/059199 | 5/2007 |
| WO | WO 2007/081955 | 7/2007 |
| WO | WO 2007/126632 | 11/2007 |
| WO | WO 2007/137226 | 11/2007 |
| WO | WO 2007/146784 | 12/2007 |
| WO | WO 2007/149348 | 12/2007 |
| WO | WO 2007/149555 | 12/2007 |
| WO | WO 2008/057261 | 5/2008 |
| WO | WO 2008/057269 | 5/2008 |
| WO | WO 2008/085825 | 7/2008 |
| WO | WO 2008/124056 | 10/2008 |
| WO | WO 2009/005714 | 1/2009 |
| WO | WO 2009/011852 | 1/2009 |
| WO | WO 2009/017680 | 2/2009 |
| WO | WO 2009/038781 | 3/2009 |

OTHER PUBLICATIONS

Pereyra, A.J., "A Simplified Surgical Procedure for the Correction of Stress Incontinence in Women," West. J. Surg., Obst. & Gynec., pp. 223-226, Jul.-Aug. 1959.

* cited by examiner

O. Int. | O. Ext.
O. Membrane.

SURGICAL ARTICLES AND METHODS FOR TREATING PELVIC CONDITIONS

PRIORITY CLAIM

The present non-provisional patent Application claims benefit from International Application No. PCT/US2007/004015, having PCT Publication No. WO 2007/097994 A2, which was filed on 16 Feb. 2007, which in turn claims priority under 35 USC §119(e) from United States Provisional Patent Application having Ser. No. 60/775,039, filed on Feb. 16, 2006, by Lund et al., titled SINGLE INCISION SLING AND METHOD OF IMPLANTING SAME IN PATIENT; United States Provisional Patent Application having Ser. No. 60/804,353, filed Jun. 9, 2006, by Westrum et al., titled SURGICAL ARTICLES AND METHODS FOR ADDRESSING URINARY INCONTINENCE; United States Provisional Patent Application having Ser. No. 60/806,073, filed Jun 28, 2006, by Anderson et al., titled SURGICAL ARTICLES AND METHODS FOR ADDRESSING URINARY INCONTINENCE; and United States Provisional Patent Application having Ser. No. 60/805,040, filed Jun. 16, 2006, by Montpetit et al., titled PELVIC FLOOR REPAIR TISSUE FIXATION, wherein the entirety of said provisional patent applications are incorporated herein by reference.

FIELD OF THE INVENTION

The invention relates to apparatus and methods for treating pelvic conditions by use of a pelvic implant to support pelvic tissue. The pelvic conditions include conditions of the female or male anatomy, and specifically include treatments of female or male urinary and fecal incontinence, and treatment of female vaginal prolapse conditions including enterocele, rectocele, cystocele, vault prolapse, and any of these conditions in combination. In particular, the present invention relates to a surgically implanted implants that support pelvic tissue and that are secured to pelvic tissue to provide that support.

BACKGROUND

Pelvic health for men and women is a medical area of increasing importance, at least in part due to an aging population. Examples of common pelvic ailments include incontinence (fecal and urinary) and pelvic tissue prolapse (e.g., female vaginal prolapse). Urinary incontinence can further be classified as including different types, such as stress incontinence, urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Urinary incontinence can be characterized by the loss or diminution in the ability to maintain the urethral sphincter closed as the bladder fills with urine. Male or female stress urinary incontinence (SUI) occurs when the patient is physically stressed.

One cause of urinary incontinence is damage to the urethral sphincter. Other causes include the loss of support of the urethral sphincter, such as can occur in males after prostatectomy or following radiation treatment, or that can occur due to pelvic accidents and aging related deterioration of muscle and connective tissue supporting the urethra. Other causes of male incontinence include bladder instability, over-flowing incontinence, and fistulas.

The female's natural support system for the urethra is a hammock-like supportive layer composed of endopelvic fascia, the anterior vaginal wall, and the arcus tendineus. Weakening and elongation of the pubourethral ligaments and the arcus tendineus fascia pelvis, and weakening of the endopelvic fascia and pubourethral prolapse of the anterior vaginal wall, may have a role in the loss of pelvic support for the urethra and a low non-anatomic position that leads to urinary incontinence.

In general, urinary continence is considered to be a function of urethral support and coaptation. For coaptation to successfully prevent or cure incontinence, the urethra must be supported and stabilized in its normal anatomic position. A number of surgical procedures and implantable medical devices have been developed over the years to provide urethral support and restore coaptation. Examples of such surgical instruments included Stamey needles, Raz needles, and Pereyra needles. See Stamey, Endoscopic Suspension of the Vesical Neck for Urinary Incontinence in Females, Ann. Surgery, pp. 465-471, October 1980; and Pereyra, A Simplified Surgical Procedure for the Correction of Stress Incontinence in Women, West. J. Surg., Obstetrics & Gynecology, pp. 243-246, July-August 1959.

One alternative surgical procedure is a pubovaginal sling procedure. A pubovaginal sling procedure is a surgical method involving the placement of a sling to stabilize or support the bladder neck or urethra. There are a variety of different sling procedures. Descriptions of different sling procedures are found in U.S. Pat. Nos. 5,112,344, 5,611,515, 5,842,478, 5,860,425, 5,899,909, 6,039,686, 6,042,534, and 6,110,101.

Some pubovaginal sling procedures extend a sling from the rectus fascia in the abdominal region to a position below the urethra and back again. The slings comprise a central portion that is adapted to support the urethra or a pelvic organ (i.e., a "support portion" or "tissue support portion"), and two extension portions bracketing the support portion, optionally a protective sheath or sheaths encasing at least the extension portions. Although complications associated with sling procedures are infrequent, they do occur. Complications include urethral obstruction, prolonged urinary retention, bladder perforations, damage to surrounding tissue, and sling erosion.

Other treatments involve implantation of a Kaufman Prosthesis, an artificial sphincter (such as the AMS-800 Urinary Control System available from American Medical Systems, Inc.), or a urethral sling procedure in which a urethral sling is inserted beneath the urethra and advanced to the retropubic space. Peripheral or extension portions of the elongated urethral sling are affixed to bone or body tissue at or near the retropubic space. A central support portion of the elongated urethral sling extends under the urethral or bladder neck to provide a platform that compresses the urethral sphincter, limits urethral distention and pelvic drop, and thereby improves coaptation. Similar attached slings or supports have been proposed for restoring proper positioning of pelvic organs, e.g., the vagina or bladder.

Elongated "self-fixating" slings have also been introduced for implantation in the body, to treat pelvic conditions such as prolapse and incontinence conditions. Self-fixating slings do not require the extension portions to be physically attached to tissue or bone. Rather, the slings rely upon tissue ingrowth into sling pores to stabilize the sling. See, for example, commonly assigned U.S. Pat. Nos. 6,382,214, 6,641,524, 6,652,450, and 6,911,003, and publications and patents cited therein. The implantation of these implants involves the use of right and left hand sling implantation tools that create transvaginal, transobturator, supra-pubic, or retro-pubic exposures or pathways. A delivery system for coupling the sling ends to ends of elongate insertion tools, to draw sling extension portions through tissue pathways, is also included. Needles of the right and left hand insertion tools described in the above-referenced 2005/0043580 patent publication have a curvature in a single plane and correspond more generally to the BioArc™ SP and SPARC™ single use sling implantation. tools sold in a kit with an elongated urethral sling by American Medical Systems, Inc.

In some sling implantation kits, the needle portion has a proximal straight portion extending from the handle and a distal curved portion terminating in a needle end or tip. As described in the above-referenced '003 patent, the kit may include more than one type of implantation tool (also, "insertion tool"). The kit may include one tool suitable for an outside-in (e.g. from the skin incision toward a vaginal incision) procedure and another that may be suitable for an inside-out (e.g. from the vaginal incision toward a skin incision) procedure. Surgeons that prefer an approach dictated by the surgeon's dominant hand can select the procedure and the appropriate implantation tool. Alternately, universal implantation tools (e.g., right and left sling implantation tools each suitable for both an inside-out and an outside-in approach) may be provided.

Optionally, a detachable protective sheath may encase some portion of an extension portion of a pelvic implant. Connectors may be attached to the ends of the extension portions for connecting with an end of an insertion tool. Generally speaking, the insertion tool ends are inserted axially into the connectors, and the extension portions of the implant are drawn through pathways trailing the connectors and needles to draw a central support portion against the pelvic tissue (e.g., the urethra) to provide support. The connectors are drawn out through skin incisions and the implant and encasing sheath are severed adjacent to the connectors.

Similar transobturator implantation procedures for implanting a pelvic implant to support a pelvic organ, e.g., the vagina, restored in proper anatomic position, are described in commonly assigned U.S. Patent Application Publication Nos. 2005/0043580 and 2005/0065395. Alternate implantation procedures for creating tissue pathways exiting the skin lateral to the anus and implanting an implant extending between the skin incisions to support a pelvic organ, e.g., the vagina, restored in proper anatomic position, are described in commonly assigned U.S. Patent Application Publication No. 2004/0039453 and in PCT Publication No. WO 03/096929. Various ways of attaching a sleeve end and implant mesh extension to a self-fixating tip are detailed in the above-referenced '450 patent, for example. Further ways of attaching extensions of an implant to an implantation tool are described in U.S. Patent Publication 2004/0087970. In each case extra incisions must be made in the patient's abdomen.

SUMMARY

The present patent application describes pelvic implants and methods for treating pelvic conditions such as incontinence (various forms such as fecal incontinence, stress urinary incontinence, urge incontinence, mixed incontinence, etc.), vaginal prolapse (including various forms such as enterocele, cystocele, rectocele, vault prolapse, etc.), among others. Embodiments of implants include a self-fixating tip at a distal end of one or more extension portions. The self-fixating tip can be placed at and secured within internal tissue of the pelvic region to support the implant end extension and pelvic tissue that is supported by the implant. As an example, a self-fixating tip can be placed at tissue of the obturator foramen (this phrase referring to tissue that lies within or spans the obturator foramen, for example the obturator internus muscle, the obturator membrane, or the obturator externus muscle). Other tissue of the pelvic region can also be locations useful for implanting a self-fixating tip. The self-fixating tips can be designed to engage a distal end of an insertion tool to allow the insertion tool to place the self-fixating tip at a desired tissue location by pushing.

Embodiments of self-fixating tips can be designed to provide desired function and performance in becoming positioned and maintaining position within tissue of the pelvic region. For example, a self-fixating tip can be designed to provide desirably low input force, desirably high pullout force, and reduced trauma caused by passage of the self-fixating tip or an associated insertion tool. A self-fixating tip may also be designed to allow for removability in situations of necessity, with reduced trauma to tissue. The self-fixating tip can be designed to minimize removal force and trauma in instances that require removal. These functional properties can result from selecting size and shape features of a self-fixating tip, such as relatively reduced overall dimensions (length or diameter) of the tip; and size, shape, and number of lateral extensions.

Exemplary methods of using a self-fixating tip attached to an implant, when implanted by use of an elongate insertion tool, allow a physician to obtain direct tactile palpation without relying on visualization or more exposure to the site. By certain previous procedures for pelvic repair, for example, a physician may have to make a deep connection or use retraction to get better exposure to deliver an implant. Pelvic surgeons inherently rely on tactile feedback and palpation of critical structures when placing these implants. The invention can eliminate the deep connection issues of certain currently-used products and methods, and allow a physician to deliver an implant to the pelvic region with less difficulty and in a manner that can be more natural to their surgical techniques.

Potential advantages related to the use of the certain of the currently-described methods and devices can include reduced overall trauma of a procedure due to one or more of: design of a self-fixating tip or insertion tool; reduced trauma caused by a self-fixating tip or associated insertion tool, due to a reduced length of tissue passages (e.g., for posterior repairs); reduced trauma based on the ability to avoid tissue passages next to critical structure; and reduced trauma due to the ability to eliminate the need for local stab (external) incisions otherwise required for needle entry and exit sites;

According to exemplary methods, a physician identifies tissue within the pelvic region to which a self-fixating tip will be secured. An insertion tool and self-fixating tip can be introduced through a medial incision to insert a permanent (plastic i.e., polypropylene or metal) or bioresorpable implant assembly that includes a self-fixating tip having one or multiple lateral extensions, to the target site. This procedure can be performed by use of a single (medial) incision.

One embodiment of implant is a urinary incontinence sling that includes a sling body, a first self-fixating tip (sometimes alternately referred to herein as an "anchor" or "anchor member") attached to a first end of the sling, and a second anchor member attached to a second end of the sling, wherein the sling is made of a single piece of mesh material.

The invention also contemplates a method of treating urinary incontinence in male and female patients. The method include creating a single medial incision (a transvaginal incision or a perineal incision) under the mid-urethra, dissecting a tissue path on each side of the incision, passing a urinary incontinence sling through the incision whereby the urinary incontinence sling is suspended between the obturator internus muscles and the sling body is positioned between the patient's urethra and vaginal wall (for a female) to provide support to the urethra. For males, a perineal incision can be made to pass the sling through the incision and suspend the sling in a manner comparable to the sling installed in the female patient anatomy. A procedure for treating male urinary incontinence may be performed with or following a prostatectomy, or otherwise.

In addition to treating urinary incontinence, the invention also contemplates methods relating to other types of pelvic floor repairs. Currently, pelvic floor repairs are surgically treated through graft augmented repairs and with kit systems that use needles to deliver a graft through an incision on the anterior and posterior vaginal wall. These current procedures address tissue, muscle and ligament weakness in the pelvic floor such as rectoceles, enteroceles, cystoceles, apical, and uterine descent.

The invention allows pelvic floor reconstruction procedures to become more minimally invasive and easier to use for all pelvic floor surgeon groups. The invention relates to a tissue fixation anchoring system that can be applied to a variety of areas of the pelvic floor: anterior repairs, posterior repairs, apical support, perineal body support (address levator hiatus openings), fecal incontinence, hysterectomy repairs with vault support by means of graft augmentation with tissue anchors into several different anatomical landmarks. These landmarks may be the white line, muscle, and fascial layers, ligament structures (sacrospinous, sacrotuberous, cardinal, round, uterosacrals, perineal and rectal ligaments, etc.) etc. The self-fixating tip can be delivered to tissue in combination with a sling, hammock, or suture thread, introduced with an elongate insertion tool directly to tissue.

Another embodiment is a method of treating urinary incontinence (e.g. SUI) in a minimally invasive manner including injecting a local anesthetic; creating only one medial (e.g., transvaginal) incision under the mid-urethra; providing a urinary incontinence sling, the sling including a sling body and a first and second anchors operably attached to the sling body; inserting the first anchor through the incision and securing the anchor into a desired location in the pelvic region; inserting the second anchor through the incision and anchoring the second anchor at a desired location in the pelvic region; positioning the sling into a desired supporting position relative to the urethra; and closing the incision. Advantageously, the entire procedure can be performed with a single incision, e.g., the transvaginal incision. There is no need for any external incision of the patient such as with other methods of installing a urethral sling.

Yet another embodiment is method of treating female urinary incontinence (e.g., SUI) in a minimally invasive manner that includes injecting a local anesthetic, creating only one transvaginal incision under the mid-urethra, inserting a urinary incontinence sling through the one transvaginal incision, anchoring the urinary incontinence sling, and closing the incision.

The present invention furthermore includes a method and apparatus for a urinary incontinence sling that is implanted through a single vaginal (or perineal for males) incision whereby the sling does not exit through another skin incision such as an abdominal or leg incision.

An aspect of the invention relates to a pelvic implant assembly that includes a support portion and an extension portion, and a self-fixating tip connected to the extension portion. The self-fixating tip includes a base comprising a proximal base end and a distal base end, the proximal base end being connected to the extension portion. The base includes an internal channel extending from the proximal base end at least partially along a length of the base toward the distal base end. The self-fixating tip further includes a fixed lateral extension extending from the base.

In another aspect, the invention relates to a pelvic implant assembly that includes a support portion and an extension portion, with a self-fixating tip connected to the extension portion. The self-fixating tip includes a base comprising proximal base end and a distal base end, the proximal base end being connected to the extension portion distal end. The self-fixating tip also includes a fixed lateral extension extending from the base. The lateral extension includes a lateral extension body bounded by edges or boundaries that include a leading edge, a trailing edge, and a length at which the lateral extension meets the base. The trailing edge has a thickness greater than the leading edge.

Another aspect of the invention includes a combination (e.g., kit, system, etc.) of an implant, as described herein, including one or more self-fixating tip. The kit also includes one or more insertion tool useful with the implant.

In another aspect, the invention relates to a method of treating a pelvic condition. The method includes providing an implant according to the current description; providing an insertion tool that includes a handle and a needle extending from the handle, the needle including a proximal end attached to the handle and a distal end, the distal end including a needle distal end that removably engages the self-fixating tip; engaging the needle distal end with the self-fixating tip, inserting the needle distal end and tip through an incision in a patient; and inserting the self-fixating tip into tissue in the pelvic region.

In another aspect the invention relates to a method of treating a pelvic condition. The method includes creating a single incision through the vagina or perineal floor; dissecting tissue beneath tissue to be supported; providing a pelvic implant according to the present description; passing the pelvic implant through the incision; and implanting the self-fixating tip at tissue of the pelvic region.

Yet another aspect of the invention relates to a method of treating a pelvic condition. The method includes: creating only one incision under the mid-urethra through the vagina or through the perineal floor; providing an implant according to the present description; inserting a self-fixating tip through the incision and anchoring the self-fixating tip within fibrous tissue; inserting a second self-fixating tip through the incision and anchoring the self-fixating tip within fibrous tissue; positioning the implant into a desired supporting position relative to tissue of the pelvic region; and closing the incision.

BRIEF DESCRIPTION OF DRAWINGS

Other features and advantages of the present invention will be seen as the following description of particular embodiments progresses in conjunction with the drawings. Drawings are schematic and not to scale.

DETAILED DESCRIPTION

Figure 1:
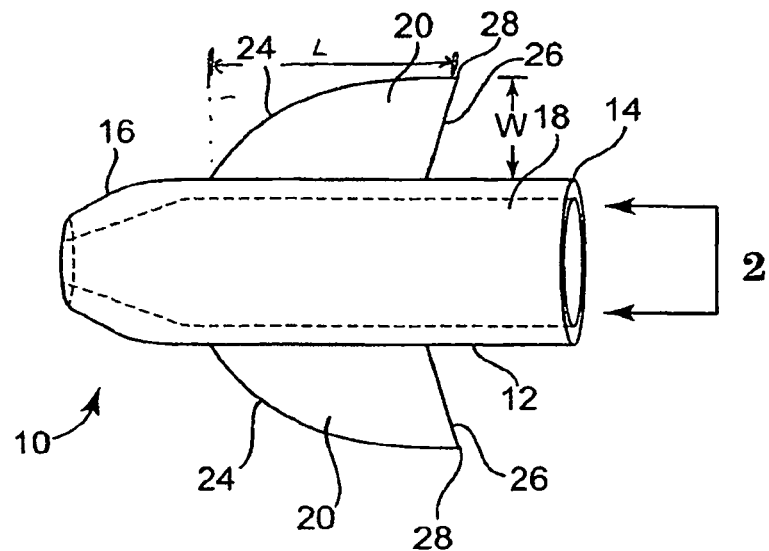
FIG. 1 illustrates a side view of an embodiment of a self-fixating tip.

The following description is meant to be illustrative only and not limiting. Other embodiments of this invention will be apparent to those of ordinary skill in the art in view of this description.

The present invention is directed to surgical instruments, assemblies, and implantable articles for treating pelvic floor disorders such as fecal or urinary incontinence, including stress urinary incontinence (SUI), prolapse, etc. According to various embodiments, a surgical implant can be used to treat a pelvic condition, including the specific examples of implanting a support member ("implant") to treat a condition such as vaginal vault prolapse or incontinence (male or female). Described are various features of surgical implants, surgical tools, surgical systems, surgical kits, and surgical methods, useful for installing implants. An implant can be implanted in a male or a female to treat disorders such as urge incontinence, mixed incontinence, overflow incontinence, functional incontinence, fecal incontinence, or for female conditions including prolapse (e.g. vaginal or uterine), enteroceles (e.g. of the uterus), rectoceles, cystocele, and anatomic hypermobility.

An implant can include a tissue support portion (or "support portion") that can be used to support pelvic tissue such as the urethra (which includes the bladder neck), vaginal tissue, etc. During use, the tissue support portion is typically placed in contact with and attached to tissue to be supported, such as with a suture. An implant can additionally include one or more extension portions (otherwise known as "end" portions or "arms") attached to the tissue support portion. Examples of pelvic implants are described in the following exemplary documents: U.S. patent application Ser. No. 10/834,943, filed Apr. 30, 2004; U.S. patent application Ser. No. 10/306,179, filed Nov. 27, 2002; U.S. patent application Ser. No. 11/347,063, filed Feb. 3, 2006; U.S. patent application Ser. No. 11/347,596, filed Feb. 3, 2006; U.S. patent application Ser. No. 11/347,553, filed Feb. 3, 2006; U.S. patent application Ser. No. 11/347,047, filed Feb. 3, 2006; U.S. patent application Ser. No. 11/346,750, filed Feb. 3, 2006; U.S. patent application Ser. No. 11/398,368, filed Apr. 5, 2005; U.S. patent application Ser. No. 11/243,802, filed Oct. 5, 2005; U.S. patent application Ser. No. 10/840,646, filed May 7, 2004; and International patent application number PCT/US2006/028828, having an International Filing Date of Jul. 25, 2006; the entireties of each of these disclosures being incorporated herein by reference.

An implant may include portions or sections that are synthetic or of biological material (e.g., porcine, cadaveric, etc.). Extension portions may be, e.g., a synthetic mesh such as a polypropylene mesh. The tissue support portion may be synthetic (e.g., a polypropylene mesh) or biologic. Examples of implant products that may be similar to those useful according to the present description, include those sold commercially by American Medical Systems, Inc., of Minnetonka Minn., under the trade names Apogee® and Perigee® for use in treating pelvic prolapse (including vaginal vault prolapse, cystocele, enterocele, etc.), and Sparc®, Bioarc®, and Monarc® for treating urinary incontinence.

Exemplary implants can include a tissue support portion for placing in contact with tissue to be supported and one or more "extension" portions, the tissue support portion being useful to support a specific type of pelvic tissue such as the urethra, bladder, or vaginal tissue (anterior, posterior, apical, etc.). The tissue support portion can be sized and shaped to contact the desired tissue when installed, e.g., as a "sling" or "hammock," to contact and support pelvic tissue. A tissue support portion that is located between two or more extension or extension portions is sometimes referred to herein as a "central support portion" or a "support portion."

Extension portions are elongate pieces of material that extend from the tissue support portion and either are or can be connected to the tissue support portion, and are useful to attach to anatomical features in the pelvic region (e.g., using a self-fixating tip) to thereby provide support for the tissue support portion and the supported tissue. One or multiple (e.g., one, two, or four) extension portions can extend from the tissue support portion as elongate "ends," "arms," or "extensions," useful to attach to tissue in the pelvic region, such as by extending through a tissue path to an internal anchoring point as described herein.

An example of a particular type of pelvic implant is the type that includes supportive portions including or consisting of a central support portion and either two, four, or six elongate extension portions extending from the central support portion. An implant that has exactly two extension portions can be of the type useful for treating, e.g., urinary incontinence, anterior vaginal prolapse, posterior vaginal prolapse; an implant having four or six extension portions can be useful for treating combinations of these conditions. The term "supportive portions" refers to portions of an implant that function to support tissue after the implant has been implanted, and specifically includes extension portions and tissue support portions, and does not include optional or appurtenant features of an implant such as a sheath or self-fixating tip or other type of connector for attaching the implant to an insertion tool.

Types of exemplary implants that can be generally useful as discussed herein can include those previously and currently used in treating pelvic conditions, including those implants referred to as urethral "slings," "strips," "mesh strips," "hammocks," among other terms for pelvic implants. Examples of implants for treating incontinence, e.g., urethral slings, can comprise a central support portion and two extension portions, and may take the form of an integral mesh strip. An exemplary urethral sling can be an integral mesh strip with supportive portions consisting of or consisting essentially of a central support portion and two extension portions. Examples of urethral slings for treating male urinary incontinence can have a widened central support portion, as discussed, for example, in Assignee's copending United States 2006/0287571 and 2006/0235262. Other exemplary urethral sling implants are described in Assignee's copending United States publication numbers 2003/0171644; 2006/0195010; 2006/0195007; among others.

Examples of implants for treating vaginal prolapse can comprise a central support portion and from two to four to six extension portions, and may take the form of an integral piece of mesh or multiple pieces of mesh attached in a modular fashion. See, e.g., Assignee's copending United States patent 2006/028828 2006/0260618; 2005/0245787; 2006/0122457; 2005/0250977; WO/2007/016083; among others.

Dimensions of an implant can be as desired and useful for any particular installation procedure, treatment, patient anatomy, and to support a specific tissue or type of tissue. Exemplary dimensions can be sufficient to allow the tissue support portion to contact tissue to be supported, and to allow extension portions to extend from the tissue support portion to a desired anatomical location to allow the extension portion be secured to anatomy of the pelvic region, to support the tissue support portion.

Dimensions of extension portions according to the invention can allow the extension portion to reach between a tissue support portion placed to support pelvic tissue (at an end of the extension portion connected to the tissue support portion) and a location at which the distal end of the extension portion attaches to pelvic tissue. A distal end of an extension portion, according to embodiments of the invention, can include a self-fixating tip that can be attached directly to pelvic tissue such as pelvic muscle, ligament, or tendon. The length of the extension portion, therefore, can be in a range that allows placement of a tissue support portion as desired to support pelvic tissue, while the self-fixating tip is installed in pelvic tissue.

As described elsewhere herein, a length of an extension portion can optionally be fixed (i.e., the extension portion does not include any form of length-adjusting mechanism), as can a length of an implant spanning from opposite self-fixating tips and including extension portions and a length or segment of tissue support portion. Alternate embodiments of implants of the invention may include adjustment or tensioning mechanisms that allow a physician to alter the length of an extension portion before, during, or after implantation. On the other hand, adjustment and tensioning mechanisms can also be excluded from embodiments of implants of the invention by selecting the length of extension portions and tissue support portions, and by adjusting for tensioning or positioning of extension portions and tissue support portions based on placement of the self-fixating tip within the pelvic tissue, selected placement including selection of the point of insertion of a self-fixating tip and depth of insertion of the self-fixating tip.

As an example, implants for treating incontinence, prolapse, or a mixture of incontinence and prolapse, can include a portion useful to support the urethra or bladder neck to address urinary incontinence. For example a urethral sling is used exclusively to support the urethra or bladder neck, and may be in the form of a mesh strip that includes a support portion implanted below the urethra or bladder neck. Implants for prolapse, especially anterior prolapse, can also include and anterior portion useful for supporting the urethra or bladder neck in the same fashion. A preferred distance between distal ends of extension portions designed to support the urethra or bladder neck can be of a total length between distal ends (e.g., self-fixating tips) to allow the combined length of extension portions and tissue support portion to extend from a right obturator foramen to a left obturator foramen, e.g., from one obturator internus muscle to the other obturator internus muscle. This length is shown at FIG. 3C as length L2 between self-fixating tips 182 (the length including the length of both of the self-fixating tips) of anterior extension portions of prolapse implant 180, and at FIG. 3B as length L2 between self-fixating tips 172 of urethral sling 170. Useful lengths of extension portions are as desired, and are exemplified elsewhere in the present description.

According to embodiments of implants and methods, a fixed-length implant or implant portion (e.g., as exemplified in all of FIGS. 3A, 3B, and 3C), including no length-adjusting mechanism, can be placed with desired positioning and effect (e.g., supportive force, approximation, or both) on pelvic tissue, by selective placement of self-fixating tips within pelvic tissue. The implant and self-fixating tips can exhibit desirable "adjustability" or "positionability" features, without the need for a length-adjusting mechanism, as follows. Each self-fixating tip of an implant or anterior implant portion can be placed within a pelvic tissue such as tissue of the obturator foramen, with properties of self-fixating tips (e.g., dimensions, pullback force, number of lateral extensions) and implant (dimensions such as length between self-fixating tips) being sufficient to allow this placement at tissue on one or both sides of the pelvic region (e.g., at opposing obturator foramen), while the tissue support portion of the implant or implant portion supports the urethra, bladder neck, vaginal tissue, etc. Desired position of the implant, the amount of approximation of the supported tissue (e.g., urethra), or the amount of supportive force placed on the supported tissue, can be achieved by selecting the placement of the self-fixating tips. Placement can include the position at which the self-fixating tip is inserted into tissue (the point of insertion) such as the placement of a tip within tissue of an obturator foramen relative to the entire area of the tissue of the obturator foramen (or another muscle, tendon, or ligament, etc.), and (if the pelvic tissue includes sufficient depth) can also include the depth to which the self-fixating tip is placed (penetrated) into pelvic tissue such as a muscle in the pelvic region, e.g., tissue of the obturator foramen or the obturator internus muscle. Each of the point of insertion, and depth of insertion, can be separately selected to result in a desired position of the implant, tension on the implant, approximation of pelvic tissue, or supportive force applied to pelvic tissue to be supported by the implant.

With regard to placement of a self-fixating tip at an obturator foramen, tissue of the obturator foramen, meaning the obturator internus muscle, the obturator membrane, and the obturator externus muscle, may have a combined thickness in the range from about 1 to about 2 centimeters. An obturator internus muscle may have a thickness in the range from 0.5 to 1 centimeter. These are rough approximations and thicknesses will depend, e.g., on anatomy of a particular patient. A self-fixating tip as described herein may be installed at any location (point of insertion) within tissue spanning an area of the obturator foramen, and at any depth of penetration into tissue of the obturator foramen, e.g., obturator internus muscle. The self-fixating tip may be passed into the obturator internus muscle, optionally into or through the obturator membrane, and optionally into the obturator externus muscle. It may be preferred to avoid penetration of the obturator membrane.

A self-fixating tip may enter tissue at an angle that is perpendicular to the tissue, or at an angle that may be as much as 30 degrees, 45 degrees, or possibly more, from perpendicular. If the self-fixating tip enters at an angle non-perpendicular to the tissue, the self-fixating tip may effectively extend through an amount of tissue that is greater than the thickness of the tissue measured at a perpendicular length or depth.

The ability to select point of insertion and depth of penetration of a self-fixating tip into a tissue is a feature of exemplary self-fixating tips and their methods of use, according to the invention, that allows a surgeon to select a location of an implant, to select an amount of tension placed on an installed implant, to place a desired amount of supportive force on a supported pelvic tissue, or combinations of these. With this feature, embodiments of the invention may avoid the need for a separate length-adjustment or tensioning mechanism, and embodiments of implants according to the invention can optionally exclude any sort of length-adjustment feature or tension-adjustment feature; these features include the use of separate implant pieces that can be secured together as desired to select a length of an extension portion or length of an implant, the use of sutures to adjust a length of an extension portion or implant, adjustable mechanical fasteners, or other cinching or mechanical mechanisms that allow a surgeon to increase or decrease a length of an extension portion or implant either before, during, or after implantation.

An example of this advantageous feature of the invention can be described with respect to placement of a urethral sling with self-fixating tips placed at opposing obturator foramen. While this example is in terms of self-fixating tips of a urethral sling placed at tissue of the obturator foramen, alternately, instead of a urethral sling, the same method and advantage can be applied to implantation of other supportive implants such as an anterior portion of an implant to treat prolapse, to support the urethra or vaginal tissue, or both, to treat a condition of vaginal prolapse, urethral incontinence, or combined vaginal prolapse and urinary incontinence. As other alternate methods an extension portion may be placed at a pelvic tissue other than the obturator foramen, such as at a different muscle, or at a ligament or tendon e.g., the arcus tendineus, sacrospinous ligament, uterosacral ligament, levator ani, etc. A tendon or ligament may have a depth less than a depth of a muscle tissue, in which case a surgeon may still select a point of entry, if not a depth of penetration, to place an implant (e.g., of fixed length) in a manner that can control location, tension, or supportive force, as stated.

According to this exemplary advantageous technique, a physician (e.g., surgeon) is able to place an implant between locations at opposite tissues of the obturator foramen to position the implant to support the urethra, without the need for an adjustment feature designed into the implant. The surgeon inserts a first self-fixating tip in tissue of one obturator foramen, preferably in the obturator internus muscle, at a desired position (i.e., point of entry relative to the total area of the obturator foramen) and a desired depth. The obturator internus muscle has enough depth to allow the self-fixating tip to be placed at a variety of depths within the thickness of the muscle. For example, the self-fixating tip may be inserted to any depth at which the lateral extensions are able to resist movement back in a direction opposite of the direction of insertion, such as by penetrating a selected depth into the obturator internus muscle. The self-fixating tip may be inserted in a direction perpendicular to the muscle or at an angle (resulting in a greater effective depth within which a self-fixating tip may be penetrated). The second self-fixating tip located on the opposite extension portion of the implant can be inserted into tissue of the opposite obturator foramen, preferably the obturator internus muscle, and the position or tension or both of the implant below the urethra, or the amount of support, approximation, or both, of the urethra provided by the sling, etc., can be selected, controlled, or adjusted by the depth and placement of the self-fixating tips within the tissue of the opposite obturator foramen.

Because these exemplary embodiments of implants and their extension portions do not require either a length-adjusting or a tension-adjusting mechanism, these embodiments of implants of the invention can include a fixed length of implant material separating two opposing self-fixating tips. A "fixed" length of material can mean that the implant does not include a length-adjusting feature such as discussed elsewhere herein, but still may exhibit an amount of elasticity or other normal mechanical properties of an implant material. A fixed length of implant material can be of a single piece of material (integral), or may be of multiple pieces secured together in a manner that does not allow further adjustment of the length. For example, multiple pieces of identical mesh material may be assembled into a single implant, before implanting the assembled implant, by sewing or otherwise attaching pieces together. Pieces of different types of mesh materials may be sewn or otherwise secured together, or pieces of synthetic material may be sewn or otherwise secured to a biologic material, in a manner that does not allow for adjustment of dimensions of the assembled implant.

The length of a urethral sling or an anterior portion of an implant, between distal ends of extension portions, can be sufficient to place opposing self-fixating tips at positions and depths of tissue of the obturator foramen, preferably without penetrating the obturator membrane, with the implant reaching between the opposing obturator foramen while supporting the urethra. Exemplary lengths of an implant or implant portion for extension below the urethra, between opposing obturator foramen, from distal end to distal end of the extensions while laying flat, can be in the range from about 6 to 15 centimeters, e.g., from 7 to 10 centimeters or from 8 to 9 centimeters or about 8.5 centimeters. (Lengths L1 and L2 of FIGS. 3B and 3C can be within these ranges.) The lengths are for male and female urethral slings, and are for anterior portions of implants for treating female prolapse or combined female prolapse and incontinence, which include an anterior portion that has a length between ends of anterior extensions portions within these same ranges.

A width of the extension portion can be as desired, such as within the range from about 1 to 1.5 centimeters.

An extension portion of an implant of the invention can include a self-fixating tip at an end of the extension portion that is distal from a tissue support portion. The self-fixating tip in general can be a structure connected to a distal end of an extension portion and that can be implanted into tissue in a manner that will maintain the position of the self-fixating tip and the attached implant. Exemplary self-fixating tips can also be designed to engage an end of an insertion tool (e.g., elongate needle, elongate tube, etc.) so the insertion tool can be used to push the self-fixating tip through tissue for implantation. The self-fixating tip may engage the insertion tool at an internal channel of the self-fixating tip, at an external location such as at the base, or at a lateral extension, as desired.

A self-fixating tip can be made out of any useful material, generally including materials that can be molded or formed to a desired structure and connected to or attached to an end of an extension portion of an implant. Useful materials can include plastics such as polyethylene, polypropylene, and other thermoplastic or thermoformable materials, as well as metals, ceramics, and other types of biocompatible and optionally bioabsorbable or bioresorbable materials. Exemplary bioabsorbable materials include, e.g., polyglycolic acid (PGA), polylactide (PLA), copolymers of PGA and PLA, A self-fixating tip also, preferably, includes one or more lateral extensions that can increase the force required to remove the self-fixating tip from tissue after insertion into the tissue, i.e. the "pullout force." At the same time, the lateral extensions can be designed to exhibit a reduced or relatively low "insertion force," which is the amount of force used to insert the self-fixating tip into tissue. The self-fixating tip is designed to be essentially permanently placed upon insertion into tissue, with the single exception that if absolutely necessary to provide desired placement of the self-fixating tip or an attached implant, the self-fixating tip may be removed by a surgeon during an implantation procedure. The self-fixating tip, and all components of the self-fixating tip, can be of combined form and dimensions to result in these functional features.

Factors that can be balanced in designing a self-fixating tip as described include insertion force and pullout force, the insertion force being preferably reduced or minimized while a pullout force allows removal of the self-fixating tip only when desired by a surgeon during an implantation procedure. Concurrently, the self-fixating tip design can attempt to minimize the amount of potential trauma caused to tissue by inserting or, when necessary, removing, a self-fixating tip. A desired combination of these factors can be achieved by selecting size, shape, and other structural features of the self-fixating tip and the elements of the self-fixating tip such as the base and lateral extensions.

Another factor that can balance the above performance properties of a self-fixating tip can be the number of lateral extensions. A self-fixating tip can have from one to a large number of lateral extensions, but it has been found that a self-fixating tip can function well with a small number of fixed lateral extensions such as two or four lateral extensions. To provide desired dimensions of a self-fixating tip, such as reduced overall length, embodiments of self-fixating tips include lateral extensions located at the same position along the longitudinal dimension (length) of the base between the proximal base end and the distal base end. A self-fixating tip that includes exactly two lateral extensions, for example, can be located opposite of each other along a length of a base, to provide desired insertion and pullout forces, especially by implanting the two lateral extensions to be oriented in fibrous tissue with the direction of the lateral extensions being not parallel to the tissue fibers, for example being perpendicular to the fibers (or "across the grain"). Also, a relatively low number of lateral extensions, such as two, can desirably reduce the amount of trauma when, as may become necessary at the discretion of a surgeon during implantation, a self-fixating tip must be withdrawn from tissue after placement.

Another feature of a self-fixating tip according to the present invention can be sizes of the base, lateral extensions, or both, to allow the self-fixating tip to be inserted into tissue at a selected depth. As an example, a lateral extension that will be placed into muscle tissue can have a length dimension (measured along a longitudinal axis of the base) that allows the self-fixating tip to be inserted into the tissue at any selected depth along the thickness of the tissue. This can mean that the length dimension of the lateral extension is shorter than the total depth of the muscle tissue.

A base of a self-fixating tip can be of any desired size, shape, and dimension (e.g., length, diameter, width). A diameter of a cylindrical base can be any useful size, for example from about 2 to about 5 millimeters. The diameter may be uniform along the length of the base, between a base proximal end and a base distal end, or a diameter may change. For example, a diameter of a base may be greater at a proximal end, and taper to a reduced diameter at a distal end, to optionally reduce insertion force or increase pullout force. The diameter or diameter profile of a base may preferably be relatively small, e.g., minimized, to reduce trauma to tissue when implanted or removed. The diameter can also be sufficient to allow placement of a desired number of lateral extensions around the perimeter of the base.

Exemplary self-fixating tips discussed herein include a cylindrical base or tapered cylindrical base, with a hollow or solid interior. Other shapes for a base may also be useful, such as blocks having square or rectangular forms when viewed in cross section along a longitudinal axis extending from a proximal base end to a distal base end. For those types of self-fixating tips, dimensions of a square or rectangular cross section can be of a range similar to the diameter of a cylindrical base, such as from about 2 to about 5 millimeters in either dimension when viewed in cross section.

As an example of a specific range of a length of a self-fixating tip, lengths (measured from the proximal base end to the distal base end along a longitudinal axis of the self-fixating tip) in the range from 0.4 to 1.0 centimeter, e.g., from 0.4 to 0.8 centimeters, or from 0.4 to 0.7 centimeters, have been found to be useful. These ranges are specifically useful for self-fixating tips that can be inserted into muscle of the obturator internus, because the relatively short length can allow the self-fixating tip to be inserted into the muscle tissue a desired depth, i.e., over a range of depths, optionally without penetrating the obturator membrane; the self-fixating tip can be of a length dimension that is less than the thickness of the muscle, so the self-fixating tip can be inserted a desired distance into the muscle.

According to exemplary embodiments, a self-fixating tip can have structure that includes a base having a proximal base end and a distal base end. The proximal base end can be connected (directly or indirectly, such as by a connective suture) to a distal end of an extension portion of an implant. The base extends from the proximal base end to the distal base end and can optionally include an internal channel extending from the proximal base end at least partially along a length of the base toward the distal base end. The optional internal channel can be designed to interact with (i.e., engage) a distal end of an insertion tool to allow the insertion tool to be used to place the self-fixating tip at a location within pelvic tissue of the patient.

Alternate embodiments of self-fixating tips do not require and can exclude an internal channel for engaging an insertion tool. These alternate embodiments may be solid, with no internal channel, and may engage an insertion tool, if desired, by any alternate form of engagement, such as, for example, by use of an insertion tool that contacts the self-fixating tip at an external location such as by grasping the base (on a side or at the face of the proximal base end) or by contacting a lateral extension.

Embodiments of self-fixating tips also include one or more lateral extension extending laterally (e.g., radially) from the base, such as from a location between the proximal end and the distal end, from a location at the distal base end, or from a location at the proximal base end.

Exemplary lateral extensions can be rigid or "fixed" relative to the base so the lateral extension does not substantially move or deflect during or after implantation. For example, a fixed lateral extension can be a lateral extension that is not substantially moveable relative to the base in a manner that certain types of known soft tissue anchor extensions are moveable, for instance between a non-deployed or non-extended position that places an extension against the base to allow insertion of the anchor into tissue with a reduced size or shape profile, and a deployed or extended position that places the extension away from the base to engage tissue and prevent movement of the self-fixating tip in a direction opposite of the direction of insertion. Alternate embodiments of lateral extensions can be moveable or deflectable, if desired, such as to allow a reduced insertion force by use of lateral extensions that deflect backward when a self-fixating tip is being pushed through tissue.

A lateral extension can have a three-dimensional form that results in a balance of the performance factors discussed herein, including insertion force, pullout force, and reduced trauma caused to tissue during insertion or in the event of a need to remove the self-fixating tip during an implantation procedure. A lateral extension can include a three-dimensional form referred to as an extension body defined as the lateral extension material between a leading edge, a trailing edge, and a boundary at which the lateral extension connects to a base; away from the boundary of the lateral extension and the base, the far lateral edge of a lateral extension may include a point of connection of the trailing edge and the leading edge, or another segment or connection may connect the leading edge with the trailing edge away from their respective connections to the base. The "leading edge" means the boundary of the lateral extension on the side of the lateral extension toward the base distal end, which is also the edge that leads the lateral extension body and contacts tissue first as the self-fixating tip is inserted into tissue by pushing. The "trailing edge" means the boundary of the lateral extension on the side of the lateral extension toward the base proximal end, which is also the edge that trails behind the lateral extension body and passes through or contacts tissue last when the self-fixating tip is inserted into tissue by pushing.

The lateral extension body can exhibit a thickness or thickness profile as desired, such as a uniform thickness or a varied thickness across the extended area of the body. For example, embodiments of implants may include a leading edge of a low profile, e.g., reduced thickness or even sharpened, to allow for reduced insertion force. According to these embodiments, the thickness of the lateral extension body can reduce gradually or taper from a central portion of the body (away from edges) in the direction of a leading edge. A leading edge, being of a reduced thickness to reduce insertion force, may optionally in addition exhibit a form that extends in a direction back toward the trailing edge, i.e., a "swept-back" leading edge, to further reduce insertion force. The shape of the leading edge may be linear or arcuate, and if arcuate may be convex or concave. Optionally the leading edge may take an arcuate convex path that sweeps back to meet the trailing edge at a single lateral extension point away from the base. E.g., see the exemplary self-fixating tip illustrated at FIG. 1.

The direction and shape of the trailing edge of a lateral extension, as the edge extends away from the base (e.g., when viewed as in FIG. 1), may be linear or arcuate, and if arcuate may be convex or concave relative to the lateral extension body. A trailing edge can be as desired, such as arcuate, straight, convex, flat, linear, rounded, tapered, sharp, blunt, etc. Optionally a trailing edge can exhibit a thickness (a thickness dimension is illustrated, e.g., at FIG. 2) to produce increased pullout force, yet that does not result in undue trauma in the event that a self-fixating tip must be removed from tissue after insertion.

Viewing the trailing edge along the longitudinal axis of the base and looking at the proximal base end (as in FIG. 2), a trailing edge can exhibit an area that includes a width (w, the distance the trailing edge extends laterally away from the base) and a thickness (t, the distance perpendicular to the width and the longitudinal axis of the self-fixating tip). An exemplary width (w, in FIG. 2) of the trailing edge can be, e.g., in the range from 0.5 to 3 millimeters.

An exemplary thickness at a trailing edge may be the same as a thickness at an interior or central portion of the lateral extension (away from the leading and trailing edges), or a thickness at a trailing edge may be a maximum thickness of the entire lateral extension, meaning for example that the thickness increases from a narrow thickness at the leading edge and widens gradually to a maximum thickness at the trailing edge. A thickness of a trailing edge can be, e.g., in the range from 0.2 to 2 millimeters, e.g., from 0.5 to 1.5 millimeters.

Based on the above-recited exemplary thickness and width dimensions, a surface area of a trailing edge may be, e.g., from the range from 0.25 to 5 square millimeters, e.g., from 0.5 to 4, or from 1 to 3 square millimeters. The surface area of the trailing edge may be concave, convex, rounded, tapered (symmetrically or toward one or the other surfaces of the lateral extension), etc. A flat surface may be preferred, to provide increased or maximum pullout force for preventing removal of the self-fixating tip after implantation.

A lateral extension can also include a third dimension that can be referred to as a "length" dimension (shown as "L" at FIG. 1). A length can be measured at a location where the lateral extension meets or extends from the base. This length dimension can become smaller as the lateral extension extends from the base. An exemplary length of a lateral extension at the location of the lateral extension meeting the base can be, e.g., from 0.5 to 5 millimeters, such as from 1 to 4 millimeters or from 1.5 to 3.5 millimeters.

In the specific example of a self-fixating tip for insertion to tissue of the obturator foramen, an exemplary length of a lateral extension can be a length that is less than the total thickness of obturator foramen tissue (i.e., the combined thickness of obturator internus muscle, obturator membrane, and obturator externus muscle); a length of a lateral extension intended to be inserted into the obturator internus muscle can be a length that is a portion of the thickness of the obturator internus, e.g., less than 1 centimeter, such as less than 0.5 centimeter.

As noted, a self-fixating tip can include multiple lateral extensions at multiple locations, either at different positions along a length of a base, at different locations around a perimeter of a base, or both. With self-fixating tips of reduced dimensions (to achieve functionality as described), a self-fixating tip may preferably include all lateral extensions originating from the same position along a length of a base, e.g., a single set of lateral extensions can be arranged around a perimeter of a base, each extending in a different direction but from the same portion of length between the proximal base end and the distal base end. See, e.g., FIGS. 1, 3A, 3B, 3C, 4, and 5.

A self-fixating tip can be connected to an extension portion of an implant in any fashion, directly by any attachment mechanism, or indirectly such as through an attachment structure such as a suture. A connection can be based on a mechanical structure, by adhesive, by a connecting suture, or by an integral connection such as by injection molding or "insert" molding (also, "overmolding") as described U.S. Publication No. 2006-0260618-A1, incorporated herein by reference. According to that description a thermoplastic or thermosetting polymer material can be insert molded or injection molded at an end of a mesh extension portion of an implant, e.g., directly to the mesh. By this method, a molded polymer can form a self-fixating tip at an end of an extension portion. The self-fixating tip can be as described herein, for example, including lateral extensions and an internal channel.

A single example of a self-fixating tip, for purposes of non-limiting illustration and explanation, is at FIG. 1. FIG. 1 shows self-fixating tip 10, including base 12 (for attachment to an implant extension end), proximal base end 14, distal base end 16, internal channel 18, and two lateral extensions 20 located on outer surfaces and on opposite sides of base 12. Tip 10 can be prepared from a biocompatible material, preferably a biocompatible material such as a biocompatible polymer, which may optionally be bioresorbable or bioabsorbable. Exemplary self-fixating tip 10 as illustrated includes internal channel 18 (optional according to the invention) which is an opening within base 12 extending from proximal end 14 toward distal end 16 along at least a portion of the total longitudinal length of base 12. Internal channel 18 is capable of receiving a distal end of an elongate needle of an insertion tool to allow tip 10 to be pushed into position within pelvic tissue during an implant installation procedure. Lateral extensions 20 include leading edge 24 and trailing edge 26. Leading edge 24 originates at base 12 and extends away from base 12 along an arcuate pathway sweeping back toward proximal base end 14, meeting trailing edge 26 at point 28. Leading edge 24 can preferably include a reduced thickness or a sharp or sharpened edge. Trailing edge 26 is shown to be relatively straight but could alternately be arcuate, concave, or convex. Trailing edge 26 has a flat surface area. Trailing edge 26 is also shown to sweep slightly back in a proximal direction, although it could alternately extend straight away from (i.e. perpendicular to) base 12 or extend away from base 12 in a direction that includes a forward component, i.e., a directional component in the direction of distal base end 16.

Figure 2:
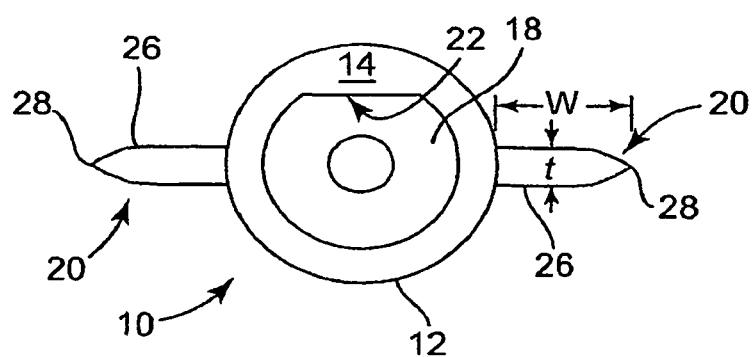
FIG. 2 illustrates an end view of an embodiment of a self-fixating tip.

Referring now to FIG. 2, self-fixating tip 10 is viewed in a direction looking at proximal base end (surface) 14 along a longitudinal axis of base 12. In this view, surface areas of lateral extensions 20 are shown as flat surfaces of approximately the area of thickness (t) by width (w). Also visible in FIG. 2 is interior surface 22 of internal channel 18 of base 12. Surface 22 functions to orient self-fixating tip 10 in a desired rotational orientation relative to a distal end of a needle of an insertion tool; the distal end of the needle can be provided with a flat surface that is complementary to surface 22. As will be appreciated, surface 22 does not need to be a flat surface but could be any other type of surface or protrusion such as a rounded surface, angled surface, key structure, edge, or other feature that can orient a self-fixating tip rotationally relative to a distal end of an insertion needle.

An insertion tool can be used to install the implant. Various types of insertion tools are known, and these types of tools and modifications thereof can be used according to this description to install an implant. Examples of useful tools include those types of tools that generally includes a thin elongate needle that attaches to a handle; a handle attached to one end (a proximal end) of the needle; and a distal end of the needle adapted to engage a self-fixating tip that allows the needle to push the self-fixating through a tissue passage and insert the self-fixating tip within tissue of the pelvic region. This class of tool can be used with a self-fixating tip that includes an internal channel designed to be engaged by a distal end of an insertion tool. Other general types of insertion tools will also be useful, but may engage a self-fixating tip in a manner that does not involve an internal channel of a self-fixating tip. These alternate insertion tools may for example contact or grasp a proximal base end of a self-fixating tip in the absence of an internal channel extending from the proximal base end toward the distal base end, such as by grasping an external surface of the base. An alternate insertion tool may contact or grasp a side of the base, a lateral extension, or any other portion of the self-fixating tip or base, in a way that allows the insertion tool to hold the self-fixating tip and insert the self-fixating tip at a desired location within tissue of the pelvic region.

Exemplary insertion tools for treatment of incontinence and vaginal prolapse are described, e.g., in U.S. patent application Ser. Nos. 10/834,943, 10/306,179; 11/347,553; 11/398,368; 10/840,646; PCT application number 2006/028828; and PCT application number 2006/0260618; among others. Tools described in those patent documents are designed for placement of an implant in a pelvic region for the treatment of prolapse, male or female incontinence, etc. The tools of the above-referenced patent documents may be curved in two or three dimensions, and may include, for example, a helical portion in three dimensions for placing an extension portion of an implant through a tissue path that passes from a region of the urethra, through an obturator foramen, to an external incision in the groin or inner thigh area. Other described insertion tools include a two-dimensional elongate needle that allows a user to place an extension portion of an implant through an external incision in the perirectal or coccyx region of the lower back and buttock area.

Exemplary insertion tools for use according to the invention can be similar to or can include features of tools described in the above-referenced patent documents. For use according to methods described herein, those insertion tools may be modified to allow the insertion tool to be used to place a self-fixating tip at tissue within the pelvic region through a tissue path that does not extend to an external incision. The insertion tool can be designed, shaped, and sized, to include an elongate inserter or needle that may be straight or that may be curved in two or three dimensions, that can be inserted through a vaginal incision (for female anatomy) or through a perineal incision (for male anatomy), and to extend from that incision to a pelvic tissue location for placement of a self-fixating tip.

Some previous insertion tools are designed to reach through a vaginal or perineal incision, through an internal tissue path and to then extend through a second external incision, e.g., at the inner groin, thigh, abdominal area, or perirectal region. As opposed to those types of insertion tools, exemplary insertion tools for use according to embodiments of presently described methods can be sized and shaped to place a self-fixating tip at an internal location of the pelvic region, and do not need to be sufficiently long to extend from a vaginal or perirectal incision to an external incision. The length can be only sufficient to reach from a vaginal or perirectal incision to an obturator foramen, for example. Alternately, the length may be only sufficient to reach from a vaginal or perirectal incision to a different muscle or tissue, such as a levator ani, coccygeous muscle, iliococcygeous muscle, arcus tendineus, sacrospinous ligament, etc., to place a self-fixating tip at one of those tissues.

According to preferred methods of the invention, a self-fixating tip may be placed into pelvic tissue that is a fibrous tissue such as muscle, ligament, or tendon, with specific examples including the arcus tendineus, the obturator internus muscle, the levator ani, and the sacrospinous ligament. Preferably, an elongate portion (e.g., elongate inserter, elongate needle, etc.) of an insertion tool can include an engagement surface for contacting a self-fixating tip, the engagement surface being in the form of any one of an internal channel or an external surface, channel, extension, or other structure. A complementary surface of a self-fixating tip (internally or at an exterior surface such but not necessarily the base), can be designed to place tip at an orientation so that lateral extensions of a self-fixating tip (i.e., the extended or "width" direction of lateral extensions) are implanted within the fibrous tissue at an orientation that places the lateral extensions in a direction that is non-parallel to the fibers of the fibrous tissue, e.g., that is at an angle of at least 45 degrees to the direction of the fibers, such as at an angle in the range from 50 to 130 degrees, or from 60 to 120 degrees, or from 70 to 110 degrees, preferably perpendicular to the fibers. In certain embodiments of the methods and devices of the invention, placing lateral extensions in such a non-parallel orientation can increase pullout force. In these embodiments, exemplary self-fixating tips can include only two lateral extensions located on opposite sides of a base.

As a specific example of the above concept of designing an insertion tool and self-fixating tip to place lateral extensions at a non-parallel orientation to fibrous tissue, this can be done for a urethral sling implant that will include a self-fixating tip placed at the obturator foramen, e.g., within the obturator internus muscle. Using a female anatomy as an example, an insertion tool and self-fixating tip can be designed to orient two lateral extensions of a self-fixating tip at an angle perpendicular to fibers of the obturator internus muscle when the needle and tip are inserted through a transvaginal incision and a tissue path leading to the obturator internus muscle. Based on that tissue path, and the direction of fibers of the obturator internus muscle, it has been found that an insertion tool that includes a curve (in two dimensions) that allows the distal end to be located at the obturator internus muscle when the needle is inserted through a vaginal incision, and that orients lateral extensions relatively perpendicular to (e.g., at an angle in the range from 75 to 105 degrees, such as from 80 to 100 degrees) a plane defined by the curve, will also cause the lateral extensions to enter the obturator internus muscle at an orientation that is substantially perpendicular to the fibers of the muscle.

Orientation of a self-fixating tip and lateral extensions relative to a needle (and tissue fibers) can be controlled using an engagement between the self-fixating tip and the needle that maintains the radial orientation of the self-fixating tip relative to the longitudinal axis of the distal end of the needle. The orientation may be maintained by any desired method, such as by one or more engaging surfaces of an internal channel of a self-fixating tip that align with one or more surfaces of a distal end of a needle. Alternately, another surface of a self-fixating tip such as a surface of the base on the proximal base end, on the outer surface of the base, or a lateral extension, may provide the desired orientation. The surfaces can be complementary, and may include flat, curved, circular, semi-circular, rounded, "keyed," or otherwise opposing surfaces that allow a surface of self-fixating tip to provide desired engagement with the insertion tool. According to certain embodiments, an internal channel of a self-fixating tip can fit over a length of a distal end of a needle of an insertion tool with a single or alternate fixed radial orientations relative to an axis of an insertion tool.

Thus, an example of a combination of insertion tool and self-fixating tip according to this description can include an elongate curved needle, hollow tube, or other "elongate inserter," curved in two dimensions, and a self-fixating tip; the distal end of the needle, tube, or inserter, and the self-fixating tip, include complementary engaging surfaces that can cause the self-fixating tip to be oriented at the distal end of the needle, tube, or inserter so that lateral extensions are oriented to be perpendicular (90 degrees, or more broadly, at an angle in the range from 80 to 100 degrees) to a plane defined by the two-dimensional curve.

The elongate inserter (e.g., needle or tube) may be of a length that allows the end of the inserter to be inserted through a perineal incision or a vaginal incision and to reach an obturator foramen, levator ani, sacrospinous ligament, or arcus tendineus. The insertion tool can be useful for placing a self-fixating tip at tissue of the obturator foramen, levator ani, sacrospinous ligament, or arcus tendineus, or other tissue of the pelvic region, preferably with lateral extensions being oriented non-parallel to fibers of a fibrous tissue.

Implants as described can be useful for treating male and female conditions of the pelvic area. Examples of specific pelvic floor disorders are fecal and urinary incontinence such as stress urinary incontinence (SUI) in both men and women, and prolapse conditions in women. The implant can be designed for a specific application with a size, shape, and number of extension portions designed to support a specific type of pelvic tissue.

According to an aspect of the invention, an implant can include one or multiple self-fixating tips at one or multiple ends of extension portions, and an implantation method can include placing the self-fixating tip or tips within tissue in the pelvic region to support the implant as the implant supports a type of pelvic tissue. The tissue can be a fibrous tissue such as a muscle (e.g., of the obturator foramen, obturator internus, obturator externus, levator ani, coccygeous, iliococcygeous), ligament (e.g., sacrospinous ligament), tendon (arcus tendineus), etc. Also preferably, but not as a requirement of the invention, a self-fixating tip can be oriented in a fibrous tissue to cause a major dimension (referred to herein as the "width") of a lateral extension to be oriented in a direction that is not parallel to the direction of the fibers.

To control the placement and degree of support of the implant relative to a tissue to be supported by the implant, the self-fixating tip can be inserted at a desired point of entry relative to the total area of the tissue, and, for tissues of sufficient thickness or depth, the self-fixating tip can be inserted to a selected depth.

A single example of a method according to the invention is a method of treating urinary incontinence by surgical implantation of a urethral sling (e.g., a single, integral, optionally uniform, woven polymeric mesh strip, with two self-fixating tips, one on each end) through a vaginal (for female anatomy) or perineal (for male anatomy) incision, along a tissue path that extends from a region of the urethra to the obturator foramen. These methods can advantageously involve only a single incision (a vaginal incision in a female or a perineal incision in a male) and can exclude the need for any additional incision. An elongate urethral sling is attached at tissue of the opposing obturator foramen by self-fixating tips at opposing distal ends of the urethral sling, with the sling positioned to pass below the urethra to support the urethra.

An exemplary method of installing a male urethral sling can include a step of creating a perineal (e.g., medial) incision at the external male perineum and creating opposing tissue paths from the medial incision, below the urethra, to the patient's left and right obturator foramen, and installing a urethral sling that includes extension portions with self-fixating tips for placement at tissue of the obturator foramen, e.g., the obturator internus muscle. Preferably, the self-fixating tip can include lateral extensions (e.g., two, of the same size and shape and form, extending in opposite directions from opposite sides of the base). When installed, lateral extensions can be oriented in a direction that is non-parallel to, e.g., substantially perpendicular to, fibers of the obturator internus muscle. The urethral sling may be placed using one or more insertion tools as described, by installing extension portions of the sling between the incision and the obturator foramen, with the middle (support) portion of the sling positioned below the urethra. The extension portions may be pushed through the tissue path at the lead of an insertion tool that engages the self-fixating tip and maintains the self-fixating tip in an orientation to enter the obturator internus muscle with lateral extensions non-parallel to the muscle fibers. The fixed orientation is maintained, and rotation is presented, also, during insertion and passage through tissue. The tissue support portion (central portion) of the urethral sling may be placed as desired to support the urethra, optionally with approximation, compression, or a combination of approximation and compression. Adjustment of the implant can be performed based on the location (point of entry) and depth of insertion of the self-fixating tips at tissue of the opposing obturator foramen. The sling may be placed below the bulbospongiosus muscle or below the corpus spongiosum, as desired. The sling may optionally include a widened central support portion that is placed to contact the corpus spongiosum, and the support portion and sling are used to approximate the urethra to improve continence, e.g., without the need for compression of the urethra. See, e.g., U.S. patent application Ser. Nos. 11/347,553 and 11/347,047.

Figure 3A:
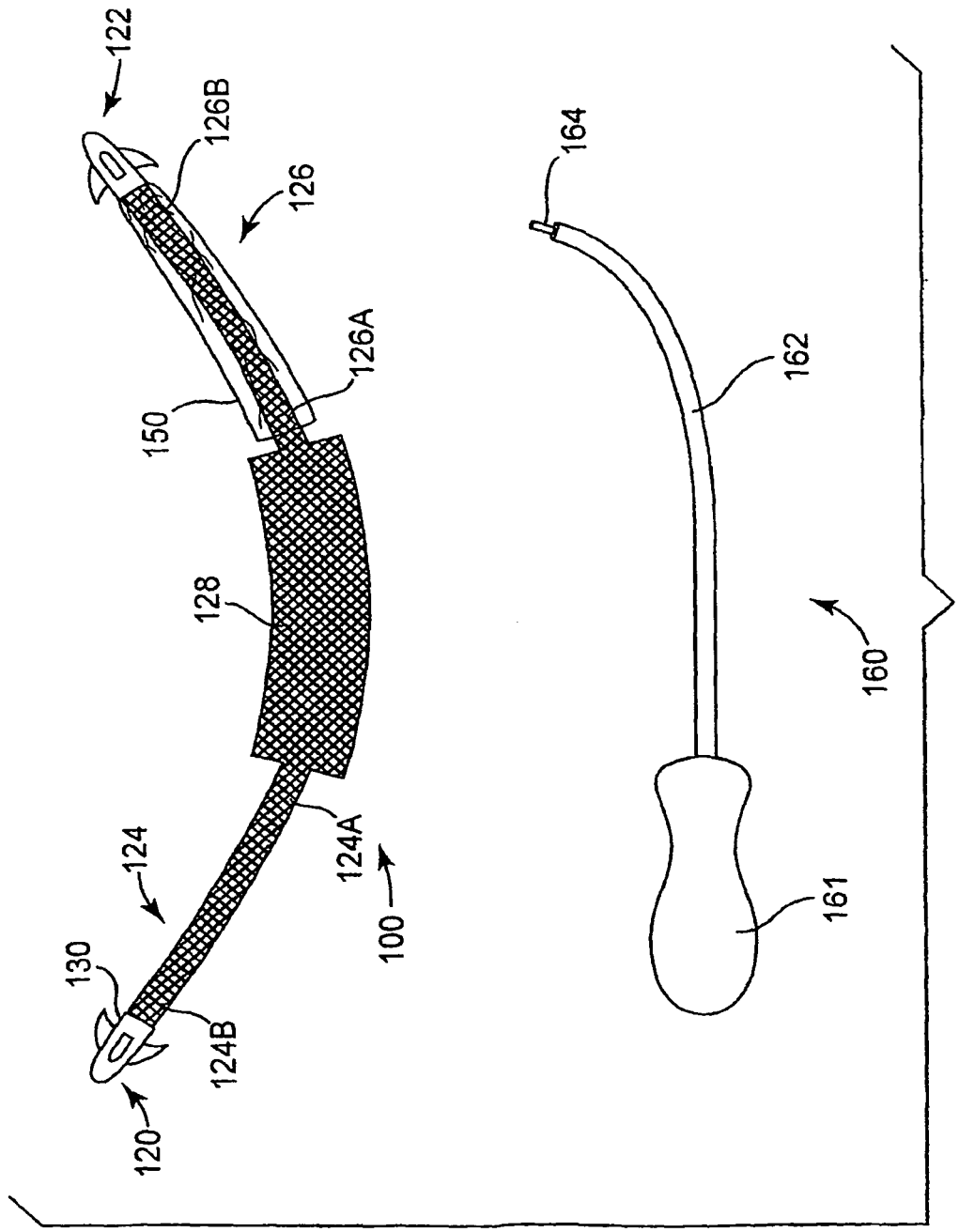
FIG. 3A illustrates an embodiment of a kit according to the invention, the kit including an implant and an insertion tool.

An embodiment of a kit according to the invention, including an insertion tool and an implant, is shown at FIG. 3A. Incontinence sling 100 can be installed to help maintain continence by supporting the urethra during times of increased abdominal pressure. The present invention also includes methods of implanting the sling 100. Sling 100 can be implanted through a single incision in the vaginal wall for females, or perineal floor for males, and attached to (e.g., anchored to) the obturator internus muscle on either side of the urethra. Only requiring one incision in the vaginal wall (for females) or perineum (for males) eliminates additional incisions such as external incisions used in some methods of implanting urethral slings, along with the scarring and invasiveness associated with the extra incisions. Sling 100 and its methods of implantation are, therefore, a reduced or "minimally" invasive treatment option for patients suffering from urinary incontinence. In alternate embodiments, sling 100 may be anchored at other locations besides the obturator internus muscle, such as, for example, the obturator membrane or the obturator externus muscle. A preferred method may be to implant sling 100 having self-fixating tips at opposing extension portions, without penetrating the obturator membrane. The present disclosure may focus on the obturator internus anchoring location, with the understanding that other anchoring locations may be selected by those of skill in the art.

Referring to FIG. 3A, sling 100 may include a first anchor (i.e., "self-fixating tip") 120, a second anchor 122, a first anchoring arm 124, a second anchoring arm 126, and a sling body ("central support portion" or "tissue support portion" 128). As illustrated, sling body 128 may be suspended between first anchoring arm 124 and second anchoring arm 126 and may be operably attached to a first end of each 124A, 126A. Second end 124B, 126B of each anchoring arm 124, 126 is attached to corresponding anchor 120, 122. The overall dimensions of the sling 100 may be 6-15 cm in length, in the range from 6 to 10, 8 to 10, 10 to 15, 10 to 12, or 12 to 15 centimeters in length, and 1-2 cm, more preferably 1-1.5 cm, in width (at the arms). The total length dimension between anchors should be at least sufficient to extend from an obturator internus muscle on one side of the urethra and into an obturator internus muscle on the opposite side of the urethra. Self-fixating tips 120 and 122 include a base, optional internal channel (not shown), and four lateral extensions, and the design is to allow self-fixating tips 120 and 122 to be implanted securely within tissue of the obturator foramen.

FIG. 3A includes a perspective view of one implant embodiment of the present invention, and the invention is not limited to the particular embodiment shown. It is understood that a large number of different sizes, shapes, and dimensions of implant (e.g., slings) will be suitable according to different embodiments of methods and implants described herein. In one embodiment the sling body 128 and anchoring arms 124, 126 are all substantially one piece (i.e., "integrated") and may be of uniform width and thickness. In such an embodiment the sling may appear as one continuous ribbon or tape. In further embodiments, sling 110 may be an assembly of two or more pieces, e.g., different pieces of mesh or combinations of mesh and a biologic material.

Sling body 128 may be made by being woven, knitted, sprayed, or punched from a blank. In one aspect of the invention, sling body 128 may include one or more woven, knitted, or inter-linked filaments or fibers that form multiple fiber junctions. The fiber junctions may be formed via weaving, knitting, braiding, or through other techniques, including combinations thereof. In addition, the size of the resultant openings or pores of the mesh may be sufficient to allow tissue in-growth and fixation within surrounding tissue.

The material used to make the sling body 128, arms 124 and 126, and anchors 120 and 122, may include a variety of different plastics or other materials that are strong but conducive to being used in the body, such as, but not limited to, polypropylene, cellulose, polyvinyl, silicone, polytetrafluoroethylene, polygalactin, Silastic, carbon-fiber, polyethylene, nylon, polyester (e.g. dacron) PLLA, acetols, EPTFE and PGA. Sling body 128, arms 124 and 126, and anchors 120 and 122, each may independently be any of resorbable, absorbable or non-absorbable; optionally, some portions may be absorbable and other portions may be non-absorbable. In further embodiments the material used to make the sling body 128 may include a non-synthetic material or a synthetic and non-synthetic blend of materials. In addition, it may be preferable that the sling body 128 be relatively elastic. In other embodiments the sling may be relatively inelastic.

Some example of commercially available materials may include MarleX™ (polypropylene) available from Bard of Covington, R.I., Prolene™ (polypropylene) and Mersilene (polyethylene terephthalate) Hernia Mesh available from Ethicon, of New Jersey, Gore-TeX™ (expanded polytetrafluoroethylene) available from W. L. Gore and associates, Phoenix, Ariz., and the polypropylene sling available in the SPARC™ sling system, available from American Medical Systems, Inc. of Minnetonka, Minn. Commercial examples of absorbable materials include Dexon™ (polyglycolic acid) available from Davis and Geck of Danbury, Conn., and Vicryl™ available from Ethicon.

First and second arms 124, 126 may likewise be made by weaving, knitting or in any of the other ways previously discussed in reference to sling body 128. First and second arms 124, 126 may be made of the same or different material as sling body 128 and may include the same or different physical characteristics, such as, for example, reabsorbability. In one embodiment, first and second anchoring arms 124, 126 may be a weave that results in a stronger or denser material than the weave used to make the sling body 128 so as to support more weight over a given surface area. In one embodiment the arms 124, 126 may not be woven. In further embodiments, sling body 128 and the first and second arms 124, 126 may be made of one continuous weave structure of the same or different weave densities.

Figure 3B:
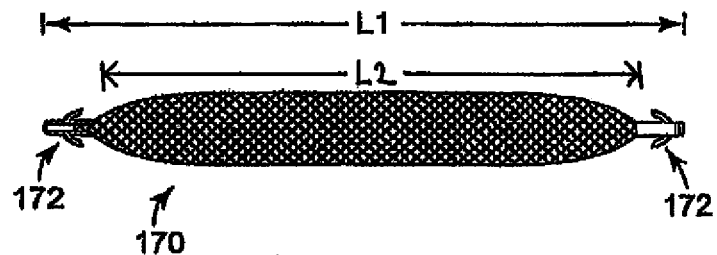
FIG. 3B illustrates an embodiment of an implant according to the invention.
Figure 3C:
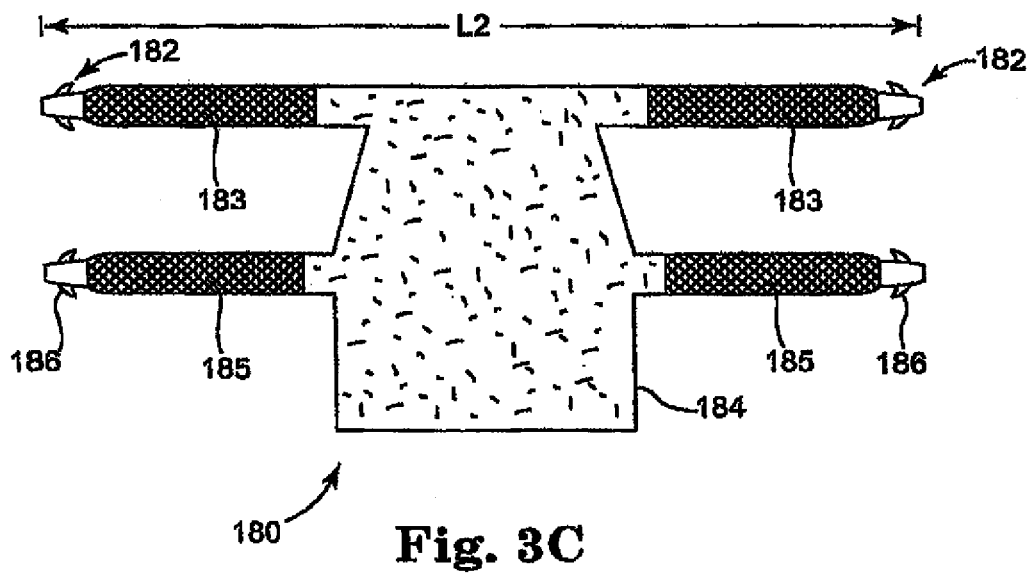
FIG. 3C illustrates an embodiment of an implant according to the invention.

FIGS. 3B and 3C illustrate alternate embodiments of implants of the invention. FIG. 3B shows urethral sling (mesh strip) 170 for supporting a male or female urethra by placement of self-fixating tips 172 at tissue of the obturator foramen. Length L1 can be, e.g., about 8.5 centimeters. FIG. 3C illustrates implant 180 for treating vaginal prolapse. Self-fixating tips 182 are at ends of anterior extension portions 183, which are each connected at their opposite ends to an anterior portion of tissue support portion 184. Posterior or central extension portions 185 are connected at one end to central portion of support portion 184, and include self-fixating tips 186 at the opposite ends. Self-fixating tips 186 may be placed at tissue of the central or posterior pelvic region such as a muscle, tendon, or ligament, e.g., a muscle of the obturator foramen, levator ani, coccygeous, iliococcygeous; sacrospinous ligament; arcus tendineus. As illustrated, central portion 184 can be a biologic material, but could alternately be a mesh or other synthetic material. Extension portions 183 and 185 are illustrated to be of synthetic mesh.

As illustrated in FIG. 3A, first and second anchors 120, 122 of an implant can be substantially identical, and, as illustrated, can be described with reference to anchor 120. Anchors 120, 122 may also be known as anchor members, fixation members, self-fixating tips, or fasteners. In one embodiment, referring also to FIGS. 4 and 5, anchor 120 may include a body (or "base") 130 with a first (distal) end 132 and a second (proximal) end 134. A number of fixation wings (or "lateral extensions") 136 may be attached to body 130 at some point or along a length between first end 132 and second end 134. In the embodiment illustrated, anchor 120 includes four fixation wings 136 spaced evenly about a perimeter of body 130. In alternate embodiments, anchor 120 may include a greater or lesser number of fixation wings 136, positioned in any desired pattern around the body 130. Fixation wings 136 may also be referred to as or may include barbs, extensions, fins, tines, spikes, teeth, or pins.

Fixation wings 136 may be as described elsewhere in the present description, and may according to certain embodiments be in the form of relatively thin (a thickness in the range of millimeters or less) wing-type structures that extend generally perpendicularly from the surface of body 130. Fixation wings 136 may extend away from body 130 to form a smoothly angled surface 138. Surface (or "edge") 138 may extend further from body 130 when traveling from first end 132 toward second end 134 in a continuous or other angular, curved, arcuate, concave, convex, or other pattern. The form of surface (or "edge") 138 can be one that allows for anchor 120 to be implanted through tissue in an implantation direction with reduced or minimal damage to the tissue, and reduced or minimal insertion force. Fixation wings 136 may further include tip 140. Tip 140 may be a barbed-like structure at the tail end of sloping surface 138. Tip 140 may allow for anchor 120 to resist being withdrawn from a desired anchoring position. Tip 140 may form a pointed tip 140 or may form a more rounded tip. In either case, tip 140 provides anchor 120 with a structure that helps to bind anchor 120 in a desired position in a pelvic tissue. As will be further discussed, anchors such as anchors 120, 122 are designed for anchoring an implant to tissue rather than bone.

Figure 4:
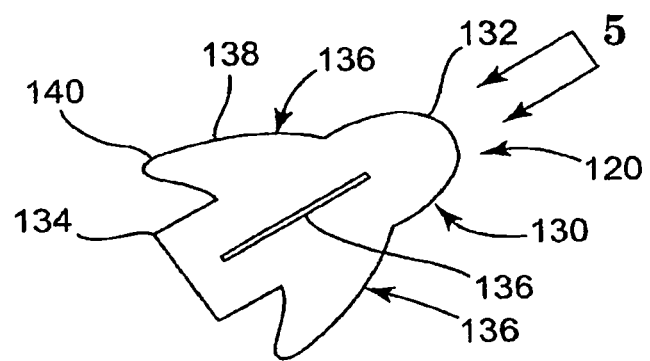
FIGS. 4 and 5 illustrate an embodiment of a self-fixating tip according to the invention.
Figure 5:
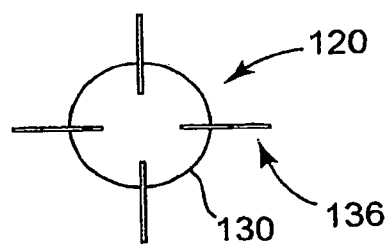

In alternate embodiments, fixation wing 136 may take other forms such as a barb, spike, (optionally fixed) etc., that can effectuate the implantation of anchors 120, 122 in the desired location. In addition, body 130 of anchor 120 may include barbs and spikes in addition to the fixation wing 136. Fixation wings 136 of FIGS. 4 and 5 are fixed, meaning not substantially moveable between different positions. Alternate embodiments of self-fixating tips (e.g., "anchors"), such as anchors 120, may include fixation wings (or "lateral extensions") 136 that are moveable, e.g., that are extended or deployed to an extended position from body 130 after anchor 120 is in the desired position, or that will otherwise move or deflect during or after insertion into tissue.

Embodiments of implants such as a sling 100 may further include a protective sleeve 150, as shown in FIG. 3A. Sleeve 150 may be a protective sheath that is placed over sling 100 or an extension portion (126) before implantation, to assist with implantation. Some slings 100 may be sufficiently robust to be inserted without a protective sleeve 150. However, in those situations wherein sling 100 requires additional structural integrity, or includes structural characteristics that may damage the tissue of the patient during passage therethrough, sleeve 150 may provide support for the implant, protection for the tissue, or both. Sleeve 150 covering mesh of sling 100 may be designed to minimize risk of contamination and to reduce abrasive "sliding" of sling 100 through tissue of a patient. Sleeve 150 may be particularly desirable when sling 100 is elastic, as sleeve 150 assists in introducing sling 100 within tissue and avoids damage to material of sling 100. After sling 100 is implanted, sleeve 150 is removed and discarded.

Preferably, protective sleeve 150 is constructed of a material that allows for visual examination of sling 100 and that affords convenient passage of sling 100 through tissue of the patient. In a preferred embodiment, sleeve 150 is made of polyethylene. Other materials including, without limitation, polypropylene, nylon, polyester, or Teflon may also be used to construct sleeve 150. Sleeve 150 should also conveniently separate from sling 100 after sling 100 is implanted, without materially changing the position or shape of sling 100.

In one embodiment, sleeve 150 may comprise two elongate, separable sections, that substantially form one continuous covering over anchor arms 124, 126 and optionally body 128 and anchors 120, 122. Optionally, portions of two sleeves 150 on opposite arms may detachably and telescopically overlap near the middle portion of the sling. Optionally, sleeve 150 may be slit or perforated or otherwise breakable (e.g. longitudinally or perpendicular to the longitudinal axis) to afford convenient separation of the separable sections into separated pieces that can be removed from a patient after implantation of an anchor.

Optionally, according to various implant embodiments, a material that forms any portion of a sling 100 may include one or more substances incorporated into the material or coated onto the material of the sling. Examples of substances may include, without limitation, drugs, hormones, antibiotics, antimicrobial substances, dyes, silicone elastomers, polyurethanes, radio plaque filaments or substances, position or length indicators, antibacterial substances, chemicals or agents, including any combinations thereof. A substance or material may be used to enhance treatment effects, reduce potential sling rejection by the body, reduce the chances of tissue erosion, allow or enhance visualization or location monitoring, indicate proper sling orientation, resist infection, or other provide other desired, useful, or advantageous effects.

In one embodiment of a method of the invention, an implant such as sling 100 (or an anterior portion of another type of implant, e.g., to treat prolapse or a combination of prolapse and incontinence) may be introduced using an "inside-out" approach to place the implant below the urethra with ends at tissue of the two opposite obturator foramen, through an incision at the vagina or perineum. The precise, final location of an implant (e.g., sling 100) will depend on a variety of factors including the particular surgical procedure performed, and any preconditions of the patient such as scar tissue or previous surgeries. For example, it may be preferred to place an implant such as sling 100 in close proximity to, but not in contact with, a mid portion of the urethra to treat incontinence. Alternately, an implant such as sling 100 may be placed near the bladder neck. The present invention is particularly suitable for placing a sling 100 or an anterior portion of a larger implant that may also treat prolapse, in a therapeutically effective position for treating any one or a combination of pelvic conditions.

For a typical procedure for treating any pelvic condition, a patient may be first placed under local, spinal, or general anesthesia. According to exemplary methods of treating a female condition of incontinence (e.g., a small, medial, transvaginal incision for treating female urinary incontinence) is made in the upper wall of the vagina under the mid-urethra. For implantation of a sling 100 to treat incontinence in a male, a perineal incision may be made instead. The incision should be large enough for the surgeon to place sling 100 through the incision using selected instruments. A desired amount of tissue may optionally be dissected on each side, for placement of sling 100. In one embodiment the tissue may be dissected approximately 1-2 centimeters in each direction away from the urethra and toward opposing locations for anchors (or "self-fixating tips") 120 (e.g., at tissue of the obturator foramen). The dissection of tissue may be as much or as little as desired, including none. The first anchor 120 is then placed through the incision and directed toward the desired anchoring position (e.g., tissue of the obturator foramen).

As previously discussed, a sling 100 or a portion of an implant may be positioned inside a sleeve 150 before the implant is inserted through the incision. In alternate embodiments, sleeve 150 may not be used or necessary, depending on surgeon preference. In one embodiment, sleeve 150 or a delivery tool can cover the woven portion but not anchors 120, 122, during implantation. In other embodiments sleeve 150 or a delivery tool may also cover anchors 120, 122. As described herein, embodiments of the invention can involve the use of various types of delivery tools to prevent an extension portion of an implant from contacting tissue of a tissue path during insertion of the extension portion through a tissue path.

In an exemplary embodiment, anchor 120 can be placed through the incision and into tissue of the obturator foramen (e.g., the obturator internus muscle, the obturator membrane, or the obturator external muscle). Anchor 120 may be driven to the desired position by the surgeon's finger or by using an insertion tool such as introducer 160.

Introducer 160 (see FIG. 3A) may be any type of insertion tool that can engage anchor 120 to drive anchor 120 through and into pelvic tissue of a desired location. Such an introducer 160 may include a durable biocompatible, curved or straight needle portion 162, made, e.g., of stainless steel, titanium, Nitinol, polymers, plastics, or other individual or combinations of materials. Handle 161 is attached at a proximal end of needle portion 162, and distal end 164 of needle portion 162 is designed to engage self-fixating tips 120 and 122, e.g., by being sized and shaped to fit within an interior channel of each tip 120, 122. Introducer 160 should have sufficient structural integrity to position anchor 120 as desired. Introducer 160 may mate with or engage anchor 120 by any manner, including fitting within an internal channel of a body or base of anchor 120, alternately on an external portion of a body or base of an anchor 120, or by interacting with fixation wings 136. Anchor 120, 122 may be situated inside or outside of sleeve 150 and introducer 160.

Once a first anchor 120 is placed into a desired position, a second anchor 122 may be inserted through the same incision and placed in a desired position on an opposite side of the patient. As with the first anchor 120, the second anchor 122 may be positioned with or without the assistance of an introducer 160 and may be placed, e.g., into tissue of the obturator foramen (obturator internus muscle, obturator membrane, obturator externus muscle). Sling body 128 may be properly oriented into the desired position in relation to the urethra. It may be desirable to ensure that the sling 100 is not twisted during implantation. Positioning of implant 100 can be accomplished by selecting the point of entry and depth of each anchor 120, 122.

Figure 6:
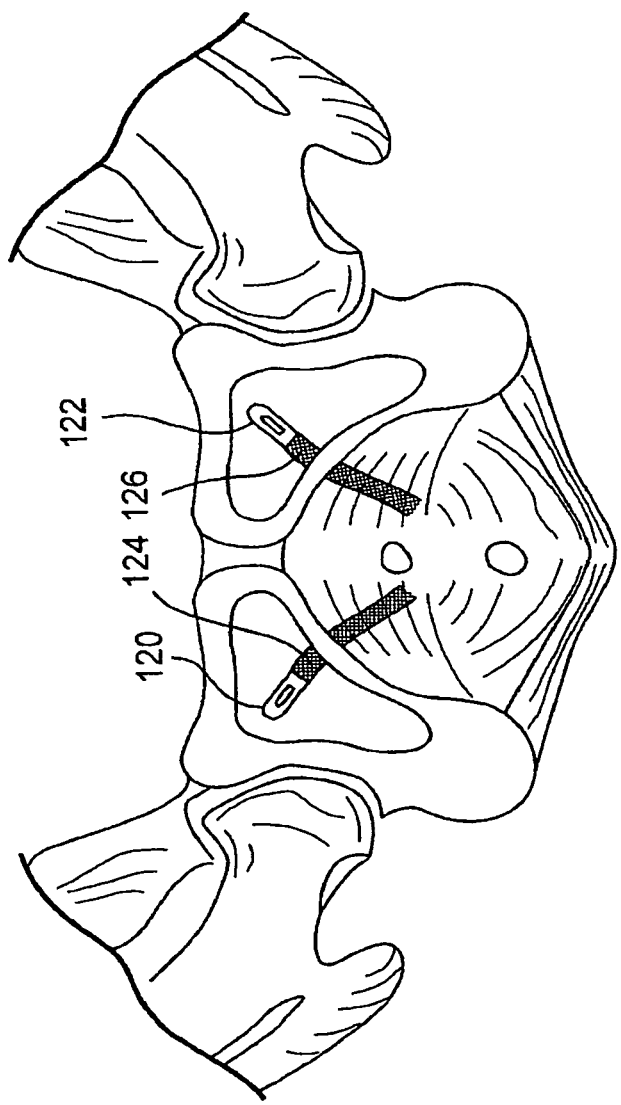
FIG. 6 illustrates exemplary placement of elements of an implant according to the invention.

FIG. 6 illustrates an example of a therapeutically effective position for a urtheral sling such as implant 100 (or, alternately, an anterior portion of an implant for treating prolapse such as implant 180 illustrated in FIG. 3C). Other positions of an implant or sling are also contemplated herein, such as positions for treating prolapse, which could alternately or additionally place extension portions and self-fixating tips through relatively more posterior tissue paths leading to posterior tissue of the pelvic region for placement of the self-fixating tips. The precise anatomical position of an implant can depend on a variety of factors including the type and degree of anatomical damage, location of significant scar tissue, and whether the procedure is combined with other procedures. Typically, an implant such as a urethral sling (e.g., sling 100) can be placed mid-urethra, without tension, but in position to support the mid-urethra. Alternately, the sling could be placed to support the bladder neck and/or UV junction. Implants for use to treat prolapse can be positioned at the middle or posterior vagina, or vaginal vault. Implants for treating fecal incontinence can be placed in the posterior portion of the pelvic region to support tissue for treating fecal incontinence.

Sling tension may be adjusted by a tension member such as a tensioning suture disclosed, for example, in U.S. Pat. No. 6,652,450. The tensioning suture may be constructed from a permanent or absorbable (i.e., bioresorbable or bioabsorbable) material. In still further embodiments, an implant such as sling 100 can be introduced with a desired amount of tension in a number of different ways, such as those discussed elsewhere in the present description that involve selected positioning of self-fixating tips.

A sleeve, 150, if present, may be removed after implantation of an implant such as sling 100 and before the adjustment of tension by a tension member such as a tensioning suture. Once the implant is positioned and optionally tensioned or adjusted, the incision may be closed.

Another embodiment of the present invention may include a kit that includes an implant (e.g., a sling such as sling 100, or any other implant as discussed herein), optionally including a sleeve 150, and an insertion tool such as introducer 160. (See FIG. 3.) The sling 100 may or may not include bioabsorbable portions or portions that induce tissue in-growth. The kit may include one or more insertion tools, which can include any features of insertion tools of the present description, and optionally and preferably can be designed to engage self-fixating tips of an implant.

Figure 7:
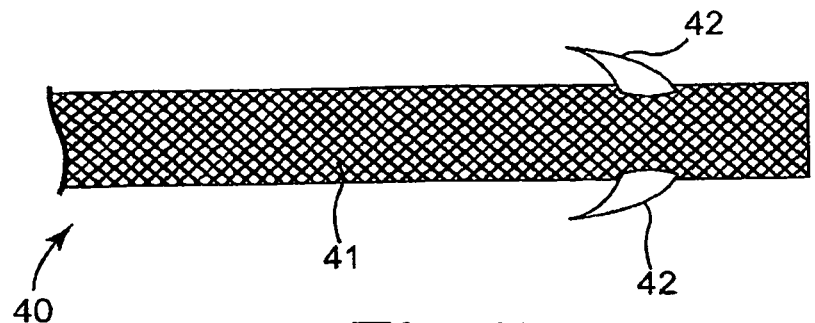
FIG. 7 illustrates an embodiment of a portion of an implant according to the invention.

As illustrated in FIG. 7, another embodiment of an implant according to the invention, implant 40, comprising mesh 41, can include anchors 42 in the form of anchoring fins (or "lateral extensions") that extend directly from locations toward the end of mesh 41. Placing fins 42 directly to mesh eliminates a discrete anchor base or anchor body while still increasing the anchoring force (pullout force) of a mesh arm. The fins 42 can be of a design described herein (e.g., of described dimensions, materials, etc.) to improve pullout force, reduce trauma, allow for a desirable insertion force, etc., and may be molded separately and attached directly to the mesh using rivets, ultrasonic welding, injection molding, or may be woven into the mesh; fins 42 may also be attached to a connecting member extending between fins 42 and connecting to mesh 41, to provide additional support between fins 42 and additional structural integrity between fins 42 and mesh 42. Fins 42 may be designed to provide anchoring at a specific anatomical level (on a membrane or fascia, for example) or for anchoring generally into soft tissue (muscle or fat).

Figure 8:
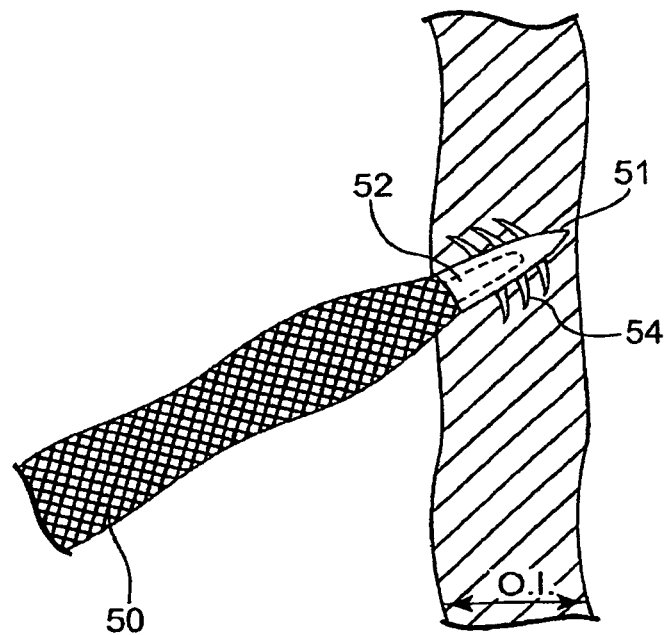
FIG. 8 illustrates exemplary placement of elements of an implant according to the invention.

As illustrated in FIG. 8, another embodiment an implant, and self-fixating tip, can be as shown. Self-fixating tip (anchors) 51 is attached at an end of mesh extension portion 50, by any of a variety of attachment mechanisms such as by injection molding anchor 51 over an extension portion end. Anchor 51, as illustrated, includes (optional) internal channel 52 for receiving an end of an insertion tool, and multiple lateral extensions 54 designed to maintain the position of anchor 51 within tissue. Lateral extensions 54 are in two opposite rows along the length of the base of anchor 51, on opposite sides of the base. Lateral extensions 54 can therefore be placed in an orientation that is non-parallel to fibers of fibrous tissue such as a muscle of the obturator foramen. To allow placement and positioning of the implant as desired, anchor 51 can be dimensioned, including its length, to be placed at a desired depth within a muscle tissue such as, e.g., the obturator internus (the muscle in FIG. 8 is shown in side view to illustrate the depth or thickness dimension of the muscle; the direction of muscle fibers is not illustrated in FIG. 8) or obturator externus. Lateral extensions 54 can also be dimensioned as described herein, to provide for one or more of desirable insertion force, pullout force, and reduced trauma.

Figure 9:
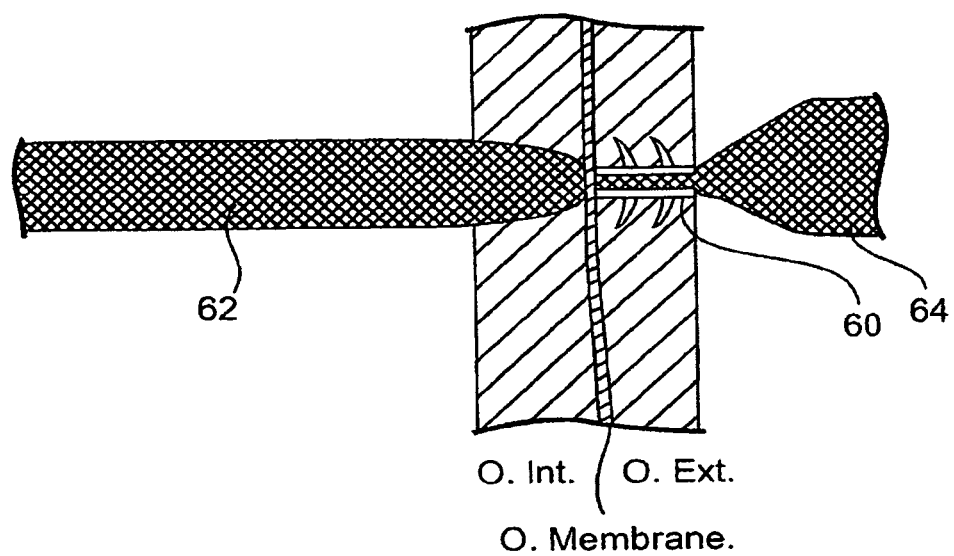
FIG. 9 illustrates exemplary placement of elements of an implant according to the invention.

As illustrated in FIG. 9, another embodiment of an implant may include anchor 60 placed at a distance along a length of an extension portion 62, optionally in a manner that allows extension portion 62 to move relative to anchor 60, e.g., to allow adjustment. In the illustration, anchor 60 has passed completely through the obturator internus muscle (o. int.), punctured the obturator membrane (o. membrane), and has been inserted within the obturator externus muscle (o. ext.). Anchor 60 may be placed at a predetermined distance from the end of a mesh extension portion 62 such that a distal portion of mesh 64 also is located beyond anchor 60. The distal portion of mesh 64 may provide greater initial anchoring and may allow for greater tissue in-growth to occur. As illustrated, anchor 60 may be a plastic or other biocompatible (optionally bioresorbable) material that is positioned and secured over the top of extension portion 62. Extension portion 62 passes through a bore that extends internally along the longitudinal dimension (length) of anchor 62 and that is sized and shaped such that the position of anchor 60 can be moveable or secured relative to the extension portion 62. Anchor 60 can be positioned and then secured to extension portion 62, e.g., by clamping anchor 60 around extension portion 62 or otherwise passing anchoring arm 62 through the bore until a desired anchor position is reached and then securing anchor 60 into position relative to extension portion 62 by use of any desirable and useful securing mechanism. In the embodiment illustrated at FIG. 9, anchor 62 causes mesh of extension portion 62 to reduce in width or narrow as the mesh passes through the internal bore of anchor 60, because of the narrow nature of anchor 60. In alternate embodiments, an anchor 62 may be of the same or similar dimensions as an extension portion 62 such that the mesh does not need to change dimensions as it passes through the bore of an anchor.

In further embodiments, other instruments, anchors, and insertion devices, as illustrated herein, may be incorporated or used with devices and methods of the present description, separately or in any combination. Various instruments and devices may aid in the insertion or retention of an implant. The devices may also be useful separately or with alternate methods or implants, as will be appreciated.

Figure 10:
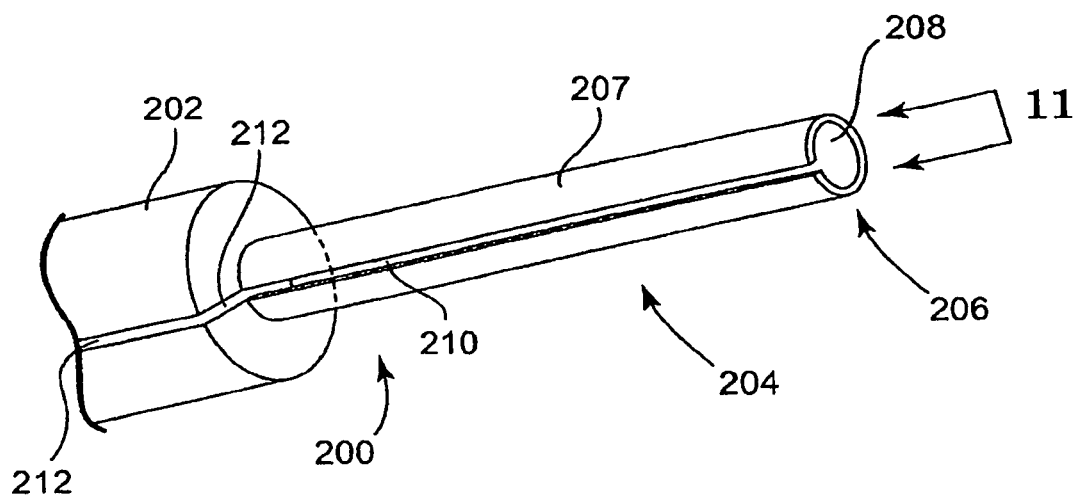
FIGS. 10 and 11 illustrate features of an embodiment of an insertion tool according to the invention.

FIGS. 10 through 14 illustrate delivery tools for assisting in insertion of an extension portion of an implant. Referring to FIG. 10, delivery tool (or "insertion tool") 200 includes handle 202 connected to hollow elongate inserter 204. Hollow elongate inserter 204 is an example of an inserter that can be used to insert an extension portion through tissue, with reduced contact between the extension portion and the tissue. For implant extensions that do not include a sheath or other removable covering (e.g., because the sheath can be difficult to remove in the absence of an external incision, as relates to exemplary methods of the present description) an insertion tool such as tool 200 can be used to reduce contact between implant and tissue, during implantation. Elongate hollow inserter 204 includes an elongate slotted tube 207 extending from handle 202 to distal end 206. An opening for inserting an implant extension portion, slot 210, extends along the length of tube 207, and also (optionally, and as illustrated) into handle 202 as slot 212. Internal bore 208 extends the length of tube 207 to form a hollow interior of tube 207 (bore 208). An extension portion of an implant can be inserted into slot 210 (and 212), to be contained by tube 207 within bore 208, for implantation. Tube 207 can act to encapsulate or otherwise protect the extension portion as the extension portion is pushed through tissue (using tool 200). Distal end 206 may be open (as illustrated), closed, or sized to receive a self-fixating tip. For example, distal end 206 can engage a self-fixating tip by contacting a complementary surface, optionally in a desired orientation. Once an extension portion is pushed into tissue of the patient, using tool 200, the extension portion can be removed from tool 200 by exiting tube 207 through slot 210. Tube 207 is shown to be straight, but may optionally be curved as desired to reach a desired tissue location.

Optionally, another insertion tool such as an elongate needle may be placed within bore 208. The second tool may include an end that engage a self-fixating tip to push the tip through bore 208 and into tissue of the pelvic region. After the self-fixating tip is located within tissue as desired, the second tool may disengage the tip and be removed from bore 208 of tube 207, and tool 200 can be removed from the tissue path.

Figure 11:
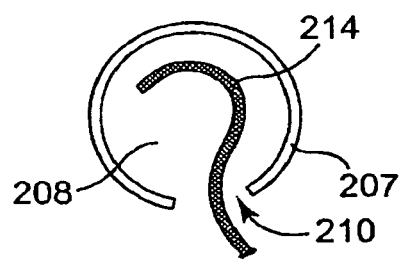

Referring now to FIG. 11, shown is an end, cross section view of elongate hollow inserter tool 200 looking in the direction from distal end 206 toward handle 202, FIG. 11 shows tool 200 from this end view, with implant 214 (e.g., mesh extension portion) shown partially within bore 208 and partially extending out through slot 210. FIG. 11 illustrates that a mesh strip (e.g., extension portion, also in an end cross-section view) may be inserted and removed from bore 218 through slot 210, prior to implanting a mesh strip (e.g., 214) into a tissue path; once the mesh strip is placed, tool 200 can be removed from the mesh strip also by passing the mesh strip (214) through slot 210.

Figure 12A:
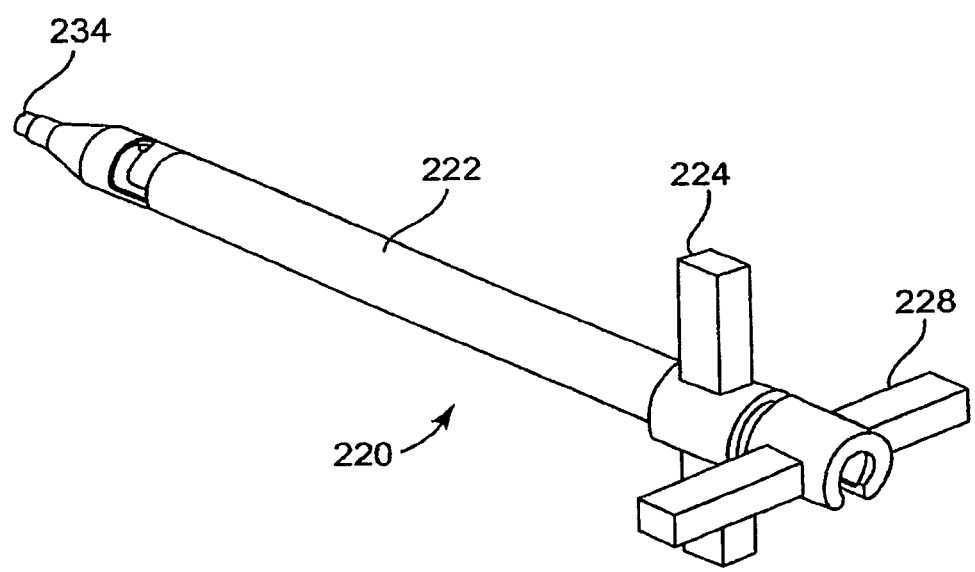
FIGS. 12A, 12B, 12C, 12D, and 12E, illustrate features of embodiments of insertion tools according to the invention.
Figure 12B:
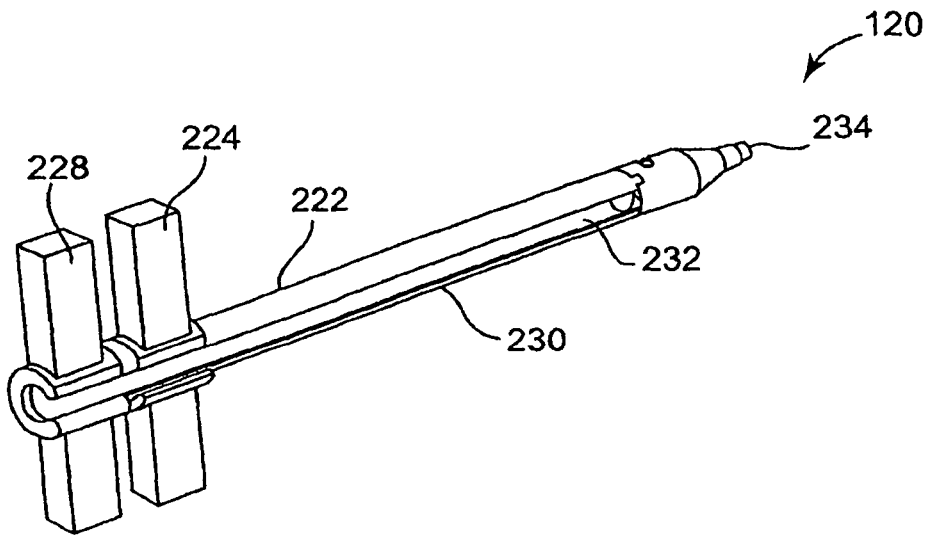
Figure 12C:
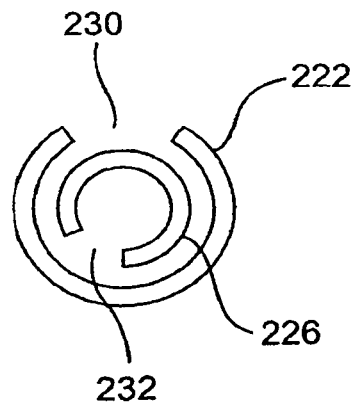
Figure 12D:
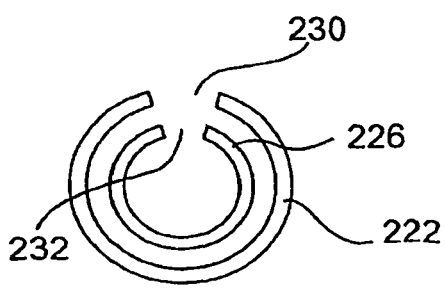

Optionally, a tool such as tool 200, designed to include a hollow interior for containing an extension portion of an implant, particularly useful for implanting an extension portion that does not include a protective sheath, can additionally include a cover that can open or close an elongate opening such as slot 210. Referring to FIG. 12A, delivery tool 220 includes an outer slotted tube 222 connected to handle 224. An inner slotted tube 226 (see FIGS. 2C and 2D), controlled by handle 228, is contained concentrically within an internal bore of outer slotted tube 222. Inner slotted tube 226 and outer slotted tube 222 each includes handles 228 and 224, respectively. Each slotted tube 222, 226 includes an internal bore to produce a hollow interior, and each tube includes a longitudinal slot (230, 232, respectively) running the entire length of each tube 222 and 226. The slotted tubes and internal bores can preferably be concentric to allow slots 230, 232 to be aligned by manipulation of handles 224 and 228. See FIGS. 12B and 12D, which show that when slots 230 and 232 are aligned, an extension portion (not shown) can be inserted through both aligned slots, into the internal space of interior tube 226. As shown in FIG. 12C, slots 230 and 232 can then be moved relative to each other to close or cover outer slot 230 by rotating the interior tube into position behind outer slot 230.

With further exemplary detail of this insertion tool embodiment, inner tube 226 may be sized and shaped such that inner tube 226 is rotatably enclosed by outer tube 222. As illustrated, inner tube 226 may be longer than outer tube 222 such that handle 228 of inner tube 226 is accessible. During placement, an extension portion (e.g., mesh strip) can be enclosed inside of inner tube 226, which is positioned inside of outer tube 222, and the handles 224 and 228 can be oriented relative to each other such that slots 230 and 232 are not aligned. See FIG. 12C. As illustrated, an anchor (self-fixating tip) 234 projects from the distal end of the inner tube 226, but in alternate embodiments inner tube 226 may instead enclose an anchor 234 during placement. Once delivery tool 220 has been inserted into the desired position, inner tube 226 and outer tube 222 are rotated relative to each other such that slots 230 and 232 are aligned and an extension portion contained within inner tube 226 can be slid out through aligned slots 230 and 232.

Figure 12E:
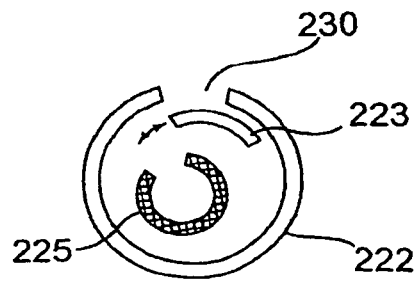

Outer tube 222 and inner tube 226 of tool 220 are shown to be straight, but may be curved if desired, e.g., by selection of a flexible material for inner tube 226. Also, a different closing mechanism could be used to close outer slot 230, such as an inner or outer cover of a smaller dimension relative to the illustrated inner tube 226. For example, FIG. 12E shows an example of an outer tube 222 and an inner cover 223, which is of a reduced size compared to inner tube 226 in terms of arclength. Inner cover 223 functions in a manner similar to inner tube 226, by being moveable (according to arrows shown in FIG. 12E) between a position that covers slot 230 and a position that does not cover slot 230 of outer tube 222. Mesh 225 is illustrated also in FIG. 12E.

Figure 13A:
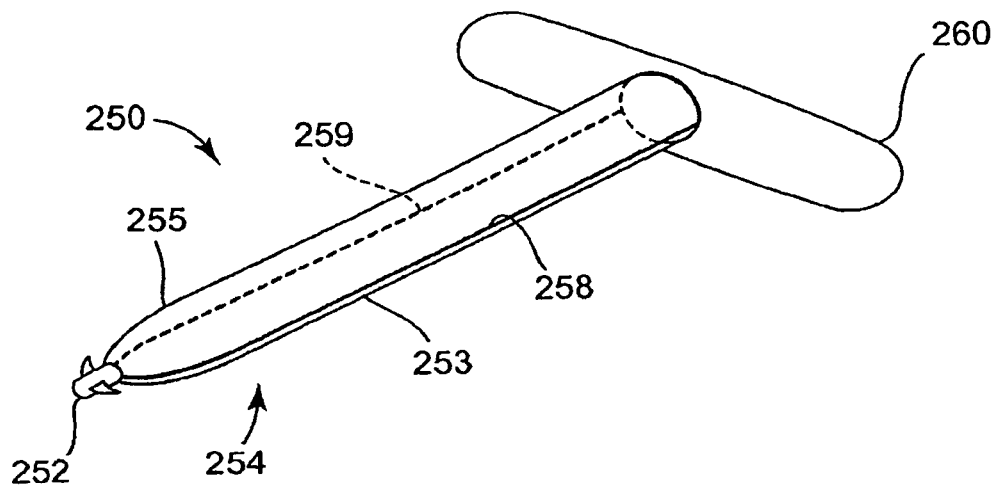
FIG. 13A and 13B, illustrate features of an embodiment of an insertion tool according to the invention.
Figure 13B:
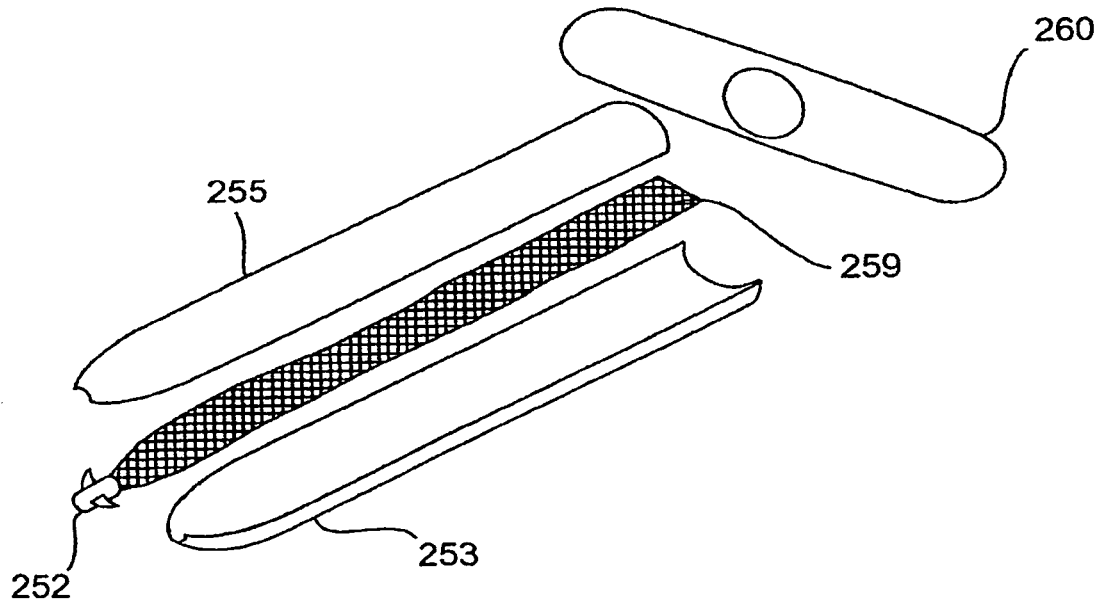

Another embodiment of an insertion tool (or "delivery tool") is illustrated at FIG. 13A. This type of tool can also be particularly useful to allow delivery of an extension portion of an implant through a tissue path to a tissue site, the extension portion not including a protective sheath, and the tissue path not leading to an external incision. In general, this type of insertion tool allows delivery at an internal tissue location, of an extension portion that does not include a sheath, by delivering the extension portion (e.g., inserting a self-fixating tip at internal tissue), then breaking pieces of the insertion tool away from The extension portion into multiple pieces that can be separated from the extension portion and individually removed from the patient.

Tool 250 as illustrated in FIG. 13A includes handle 260, elongate body 254 extending distally along a length from handle 260. Body 254 includes first and second peel lines (or, "separation lines" or "break lines") 258, 259 along a longitudinal length (peel line 259 is shown as dashed line 259 because peel line 259 is located on the far side of body 254). Peel lines 258, 259 may be a tear line or break line, or other separable engagement along which two separate pieces of elongate body 254 come together when assembled. Two or more separable pieces 253, 255 Of body 254 are assembled to allow tool 250 to function during implantation of an implant, and then can be broken apart or disassembled to remove the pieces after a self-fixating tip has been inserted into pelvic tissue.

As illustrated, two separate pieces (253 and 255) of body 254 are of substantially equal and complementary sizes, i.e., each constitute half of body 254, to produce a hollow, elongate, cylindrical body from pieces 253 and 255 when assembled, with an open interior for locating an extension portion of an implant; illustrated pieces 253, 255, are substantially opposite sides (halves) of body 254 that are designed allow body 254 to break apart and separate into two sections along its length, for removal of separated pieces 253, 255, after implantation of the extension portion. Handle 260 can be removed from the proximal end of body 254 to allow pieces 253, 255 to be dis-assembled. Handle 260 may be integral (as illustrated), or may likewise separate into two pieces. As in the previous delivery tools, body 254, when assembled, includes a bore therethrough that encapsulates or encloses an extension portion of an implant (e.g., a urethral sling) during placement. Moreover, an anchor (252) may or may not extend from a distal end of the body 254 during placement. Once delivery tool 250 is in position, handle 260 is separated into two sections (253, 255) and body 254 is withdrawn and simultaneously peeled, leaving an extension portion in the desired position.

An insertion tool according to the invention can optionally include a mechanism by which a self-fixating tip can be securely and releasable engaged with a distal end of an insertion tool such that a self-fixating tip can be selectively secured to the distal end mechanically, then released; this contrasts with, for example, a simple slidable engagement that involves only a distal end of an insertion tool engaging a surface (e.g., inner channel) of a self-fixating tip in the absence of any securing mechanism. With a releasable engagement, a self-fixating tip can be removed from the distal end by releasing the engagement (e.g., mechanical engagement) by movement of an actuator at the proximal end of the insertion tool, such as at the handle.

For example, an internal channel (or external surface) of a self-fixating tip base can include an engaging surface designed to engage a mechanism at the distal tip (i.e., distal end) of an insertion tool while the self-fixating tip is placed at, on, or over the distal end of the insertion tool. As an example, an internal or external surface of a self-fixating tip can include a depression, ring, edge, or ledge, that can be rounded, angular, etc. A mechanical detent such as a pin, ball, spring, deflector, or other surface or extension located at the distal end of the insertion tool can be moved, deflected, or extended relative to the distal end of the insertion tool to contact a surface of the self-fixating tip, such as the depression, ring, edge, or ledge, etc., to securely and releasably hold the self-fixating tip at the distal end of the insertion tool and prevent removal of the tip from the distal end, until removal is desired. The detent (extended, moved, or deflected surface, spring, deflector, pin, or ball, etc.) can be cause to extend from the distal end of the insertion tool by actuating a trigger or other mechanism located at the handle of the insertion tool. Upon placement of the self-fixating tip at a desired location during a surgical implantation procedure, the insertion tool operator can release the self-fixating tip by use of the trigger or other mechanism at the handle to disengage the detent and cause the tip to become loose. The insertion tool can then be removed from the tissue path, and the self-fixating tip can remain in a desired implanted location. An example of such tool is illustrated that FIGS. 14A, 14B, and 14C.

Figure 14A:
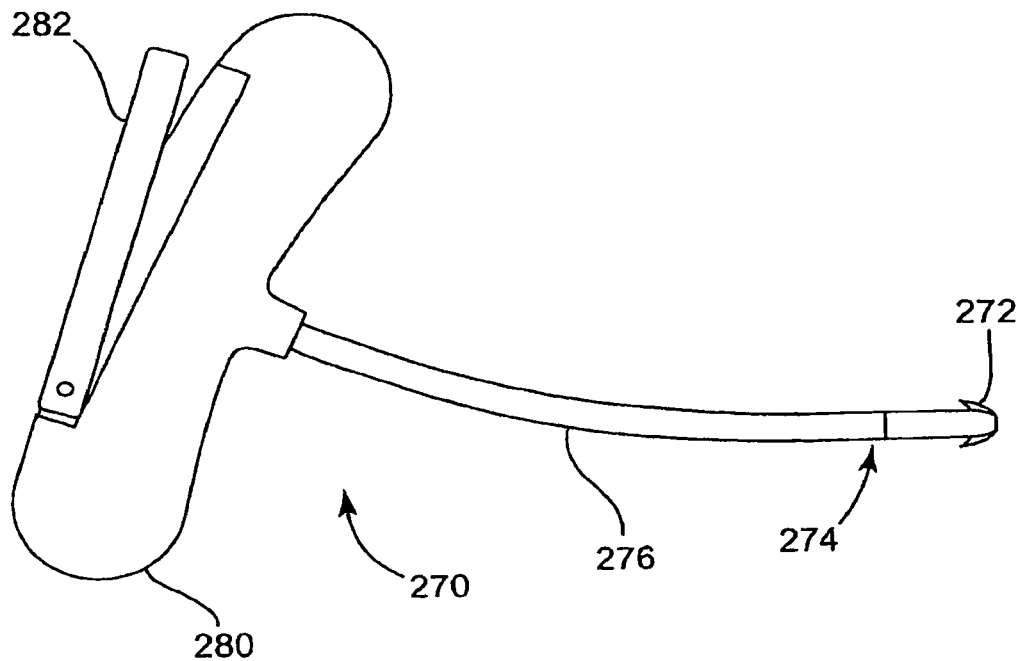
FIGS. 14A, 14B, and 14C illustrate features of an embodiment of an insertion tool according to the invention.
Figure 14B:
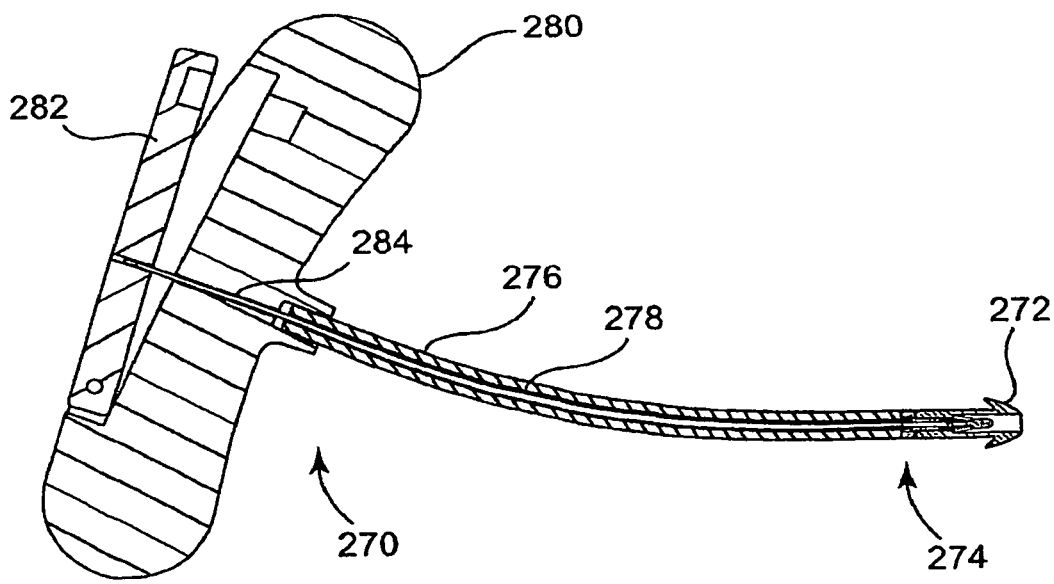
Figure 14C:
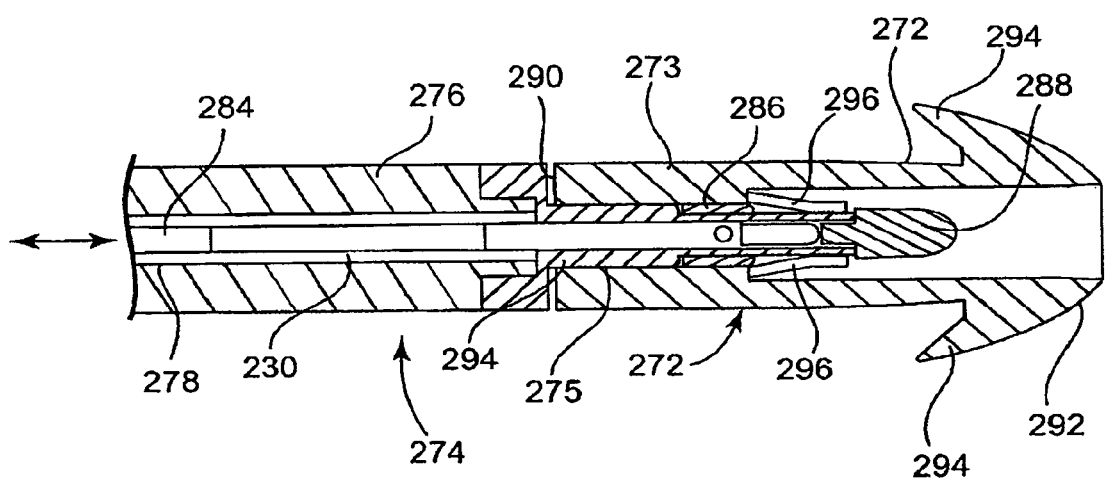

FIGS. 14A through 14C illustrate a lever-activated delivery tool 270 that includes a lever that can activate and de-activate a detent at distal end 274 of tool 270, the detent being capable of retaining self-fixating tip 272 at distal end 274 during an implantation procedure, and releasing tip 272 as desired upon placement. Lever 282 controls the detent which may be, e.g., a mechanical engagement mechanism that allows delivery tool 270 to securely engage and releasably dis-engage anchor 272 from distal end 274.

In more detail, tool 270 includes handle 280, having lever 282 operably positioned (hinged) on handle 280. Elongate hollow tube 276 extends distally from handle 280 and includes bore 278 therethrough, from handle 280 to distal end 274. Push rod 284 is fitted through bore 278. Anchor 272 is fitted into or onto distal end 274 of tube 276. A mesh sling or extension portion (not shown) of an implant can be attached to self-fixating tip 272; an extension portion or mesh sling may be attached directly to anchor 272 such that the extension portion or mesh sling drags along the outside of tube 276 during insertion through a tissue path. In alternate embodiments a sling or extension portion may be positioned in a separate bore of tube 276. If anchor 272 is disposed inside of tube 276, a proximal end of the mesh strip or extension portion can exit the tool at a proximal end of tube 276, or at the proximal side (trigger-side as illustrated) or distal side of handle 280.

During insertion, when delivery tool 270 and tip 272 have been placed in a desired position, lever 282 may be moved to cause push rod 284 to move through bore 278. At distal end 274, movement of push rod 284 causes release of a detent that allows tip 272 to be easily released from distal end 274.

Any releasable engagement and detent mechanism that is capable of holding a self-fixating tip at a distal end of an insertion tool may be useful according to the present description. As will be appreciated, a number of different structures, mechanisms, collars, locking arms, or other mechanical features may be integrated into an insertion tool such as tool 270 to effectuate holding and release of an anchor during implantation. A detent or other releasable attachment between a distal end of an insertion tool and a self-fixating tip may operate on principles of a friction fit, a snap fit, a twist connection, a rotating connection, a moveable engagement, or any other structure of method known to those in the mechanical engagement, holding, and release arts. The engagement may contact any portion of a self-fixating tip, such as an internal bore of a base, an external surface of a base, a lateral extension, etc. FIG. 14C shows details of a single embodiment of a useful mechanical detent mechanism; this example is not limiting and other types of engagement mechanisms can be used instead.

Referring now to FIGS. 14A-C, self-fixating tip 272 is located at distal end 274 of tool 270. Self-fixating tip 272 includes internal channel 275, base 273, proximal end 290, distal end 292, and lateral extensions 294. Distal end 274 of insertion tool 270 includes tube 276, bore 278, and push rod 284. The far distal end of push rod 284 extends to a location within internal channel 275 of self-fixating tip 272. At that portion of push rod 285 is connected a collar 286 and an enlarged tip 288; in this exemplary illustration, collar 286 can be moveable relative to pushrod 284, and enlarged tip 288 can be stationary relative to pushrod 284.

Within internal channel 275 of self-fixating tip 272, connected to internal channel 275, are mechanical detents, "arms" or springs 296, biased to contact push rod 285. As will be appreciated, movement of collars 286 distally will cause collar 286 to engage springs 296, causing springs 296 to be pushed away from contacting pushrod 285 and creating an aperture that will allow enlarged tip 288 to be moved proximally through opened springs 296. Collars 286 are moved away from pushrod 285 a sufficient distance to create an opening between springs 296 large enough for enlarged tip 288 to pass through the opening while moving in a proximal direction, thereby releasing self-fixating tip 272 from distal end 274 of the insertion tool.

Figure 15:
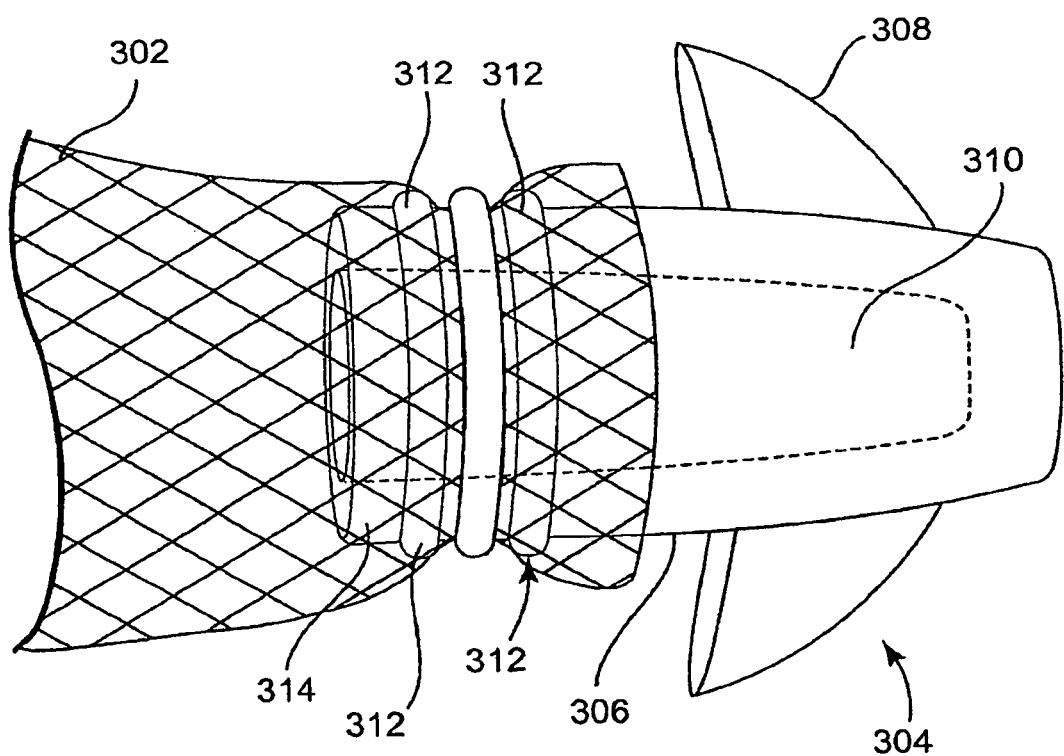
FIG. 15 illustrates an embodiment of a portion of an implant according to the invention.

FIG. 15 illustrates an embodiment of a method of connecting an end of mesh extension portion 302 to a self-fixating tip 304. Referring to FIG. 15, self-fixating tip 304 includes base 306, lateral extensions 308, and internal channel 310. Ribs 312 are located toward proximal end 314 of tip 306. Ribs 312 are ridges or bumps or extensions on the outer surface of tip 306, and (as illustrated) extend around a full circumference of base 302. Ribs 312 are not required to be continuous around the circumference of base 302, but could be intermittent or interrupted. Mesh extension portion 302 contacts proximal end 314 around the exterior surface of base 306. According to this embodiment of a self-fixating tip, ridges 312 allow mesh 302 to be connected to tip 304 by a suture or other mechanical fastening device wrapped around mesh 302, placed about base 306, the suture or fastener being wrapped around base 306 at a location between ribs 312.

Figure 16A:
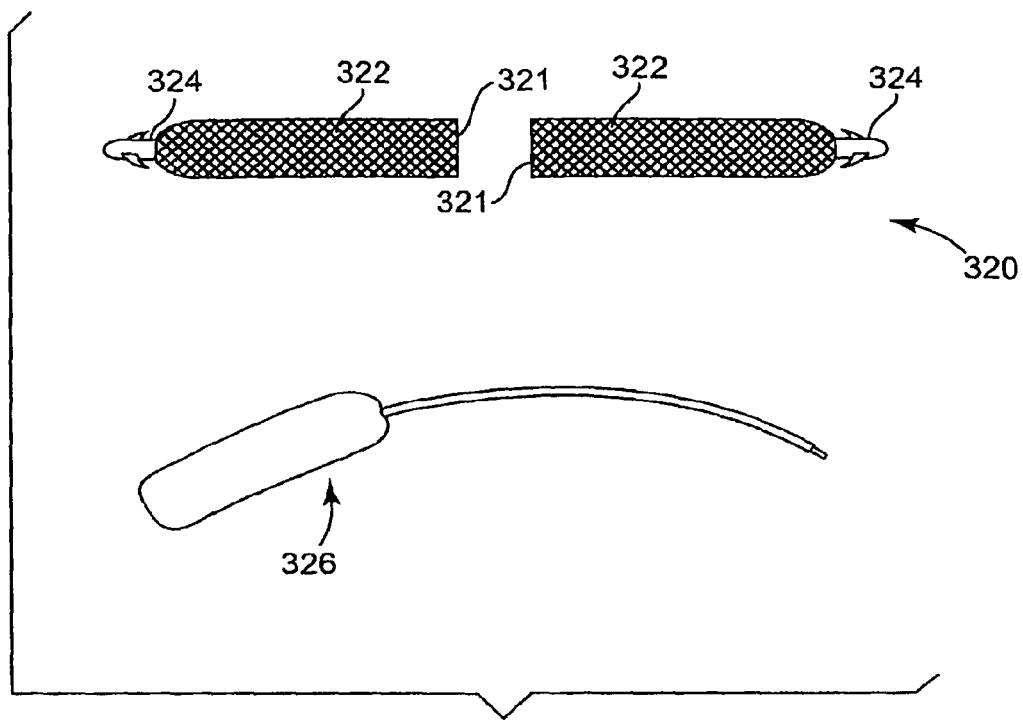
FIG. 16A illustrates an embodiment of a kit according to the invention, the kit including an implant and an insertion tool.
Figure 17:
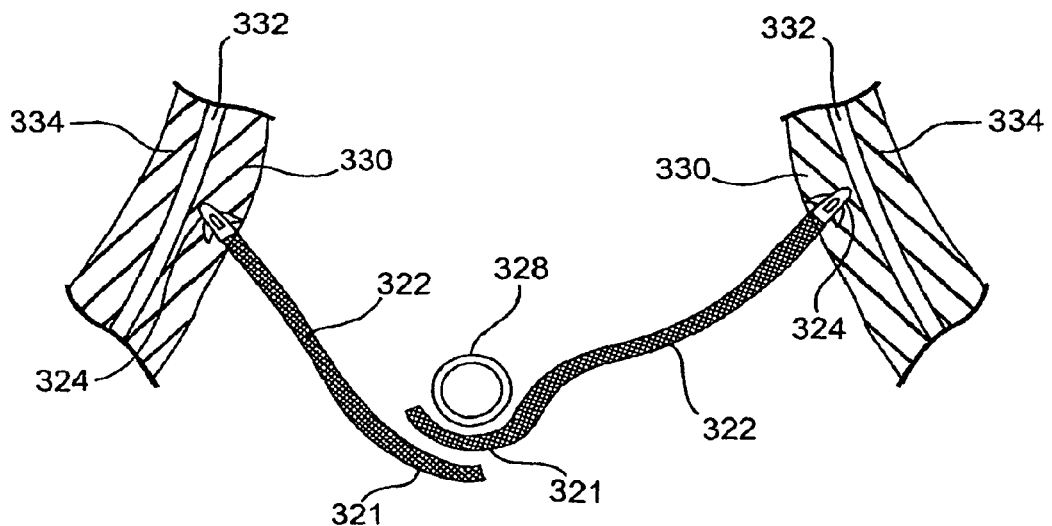
FIG. 17 illustrates exemplary placement of elements of an implant according to the invention.

In another embodiment of an implant according to the invention, an implant for treating a pelvic condition such as incontinence, prolapse, or a combined condition of incontinence and prolapse, may be assembled from separate pieces, e.g., as a modular assembly of parts, which can be advantageous for reasons including flexibility in placement of the different pieces and in sizing of an assembled modular implant. FIGS. 16 and 17 illustrate implant 320 that includes two support portions 322, each including a self-fixating tip 324 (as described herein). Also illustrated is an insertion tool 326 (as described herein) that can be useful in combination with implant 320, e.g., in the form of a kit. Implant 320 can be placed as two different sections and then connected together at a desired position and tension to form a single implant from the combined pieces. Each of the two portions of implant 320 may be placed with any insertion tool such as tool 326, or any alternate insertion tool described herein. Once each sling section 322 is placed, sling sections 322 may be attached at their connecting ends 321 by use of any fastening mechanism, such as by clips, sutures, or other methods known to those in the art or developed in the future.

FIG. 17 show implant 320 after implantation. Each tip 324 is secured within pelvic tissue, such as obturator internus muscle 330, and mesh portions 322 extend through tissue paths to meet at connecting ends 321 below urethra 328, where connecting ends 321 can be attached together while a desired amount of tension is placed on urethra 328. Obturator membrane 332 and obturator externus muscle 334 are also shown.

Figure 16B:
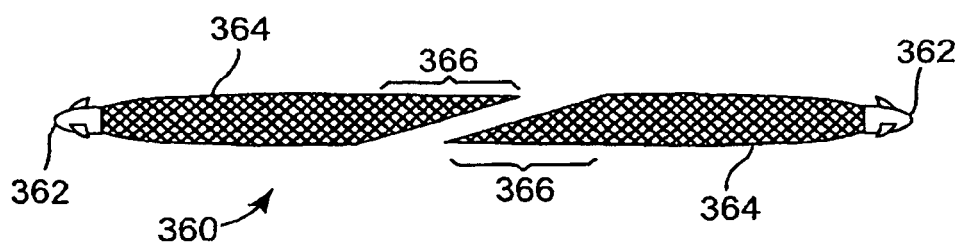
FIGS. 16B and 16C illustrate embodiments of implants according to the invention.

Another example of a multi-piece, e.g., modular, implant is shown at FIG. 16B. Implant 360 includes two support portions 364, each including a self-fixating tip 362 (as described herein). Each support portion 364 includes a connecting end 366, which includes a non-perpendicular cut, such as a slanted cut (as illustrated). The use of a non-perpendicular (e.g., slanted) cut can result in a reduced amount of overlapping material underneath a urethra upon implantation of portions 364 and connection together of connecting ends 366. A reduced amount of implant material (e.g., mesh) present below the urethra can reduce the bulk of the supportive material below the urethra and can reduce the chance of erosion. Implant 360 can be placed as two different sections and then connected together at a desired position and tension to form a single implant from combined portions 364. Once each sling portion 364 is placed, sling portions 364 may be attached at their connecting ends 366 by use of any fastening mechanism, such as by clips, sutures, or other methods known to those in the art or developed in the future.

Figure 16C:
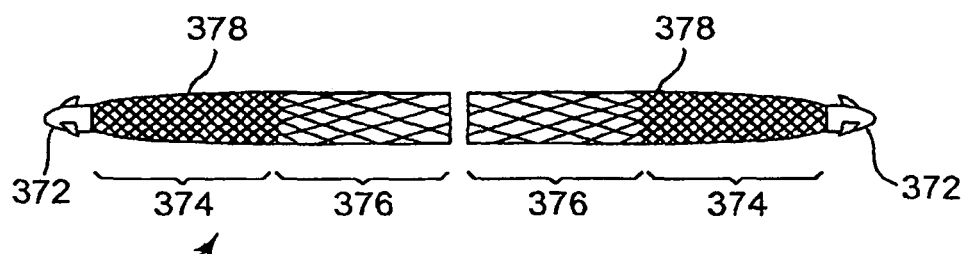

Another example of a multi-piece, e.g., modular, implant is shown at FIG. 16C. Implant 370 includes two support portions 378, each including a self-fixating tip 372 (as described herein). Each support portion 378 includes a proximal portion 376 and distal portion 374. Proximal portion 376 is the portion of the implant material that will be located below the urethra upon implantation, and distal portion 374 connects proximal portion 376 to self-fixating tip 372. According to this embodiment of the invention, proximal portion 376 is made of support material that is of a density (mass per volume) that is less than the density of distal portion 374. The use of a reduced density material for proximal portions 376, which can be connected below the urethra, cut can result in a reduced amount of overlapping material underneath a urethra upon implantation of portions 378 and connection together of proximal portions 376. A reduced amount of implant material (e.g., mesh) present below the urethra can reduce the bulk of the supportive material below the urethra and can reduce the chance of erosion. Implant 370 can be placed as two different sections and then connected together at a desired position and tension to form a single implant from combined portions 378. Once each sling portion 378 is placed, sling portions 378 may be attached at their proximal portions 376 by use of any fastening mechanism, such as by clips, sutures, or other methods known to those in the art or developed in the future.

Figure 18:
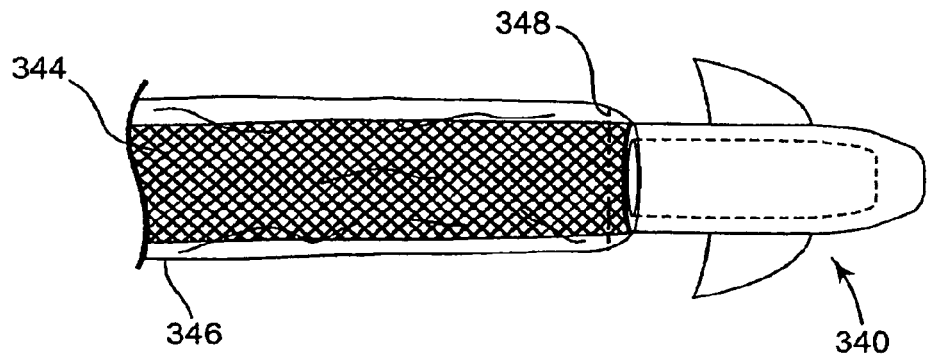
FIG. 18 illustrates an embodiment of a portion of an implant according to the invention.

In a further embodiment of an implant shown at FIG. 18, an implant may include an anchor 340, mesh extension portion 344, and break-away plastic sheath 346. Perforations 348 are located on sheath 346 at a position near anchor 340. A breakable connection such as perforations 348 allows sheath 346 to be removed, e.g., broken or torn away from, the perforated connection near anchor 340 after anchor 340 is implanted into pelvic tissue. The size and amount of perforations 348 can be selected to cause sheath 346 to break at perforations 348 instead of moving anchor 340 when sheath 346 is pulled.

Alternately or in addition to perforations 348, an elongate wire, needle, string, or other connection (not shown), can extend from the location of perforations 348 to a location available to a physician during implantation, so that the connection can cause sheath 346 to be broken near anchor 340 as desired. According to one specific example of this design, a needle with bend or a T-shaped tip may be situated within sheath 346 and positioned next to a perforated or otherwise weakened section of the sheath, e.g., near self-fixating tip 340. When anchor 340 has been implanted at a desired position within tissue, the needle may be spun, turned, or otherwise moved or manipulated to break sheath 346 at a location near anchor 340 and release sheath 346 from anchor 340. In further embodiments the needle and sheath 346 may be integrally formed so that when the needle is twisted or pulled, the end of 346 sheath twists relative to anchor 340 and the torque force breaks sheath 346 near anchor 340.

Figure 19:
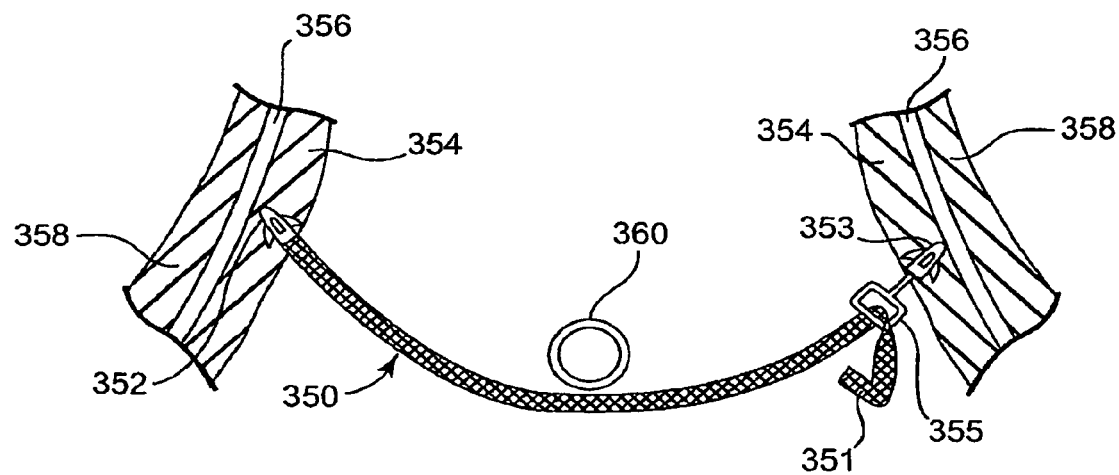
FIG. 19 illustrates exemplary placement of elements of an implant according to the invention.

Embodiments of implants can also allow for adjusting the position or tension of an implant after implantation. An example is shown at FIG. 19. Urethral sling 350 includes anchors 352 and 353 placed at opposing obturator internus muscles 354. Obturator membrane 356 and obturator externus muscle 358 are also shown. Implant 350 can be affixed using first anchor 352, which is fixed to one end of implant 350, and is adjustably attached to anchor 353 on the other end. Anchors 352 and 353 may be self-fixating tips as described. However, anchor 353 includes a loop or slot 355 through which end 351 of implant 350 can be adjustably located, then secured into place upon positioning or adjustment. Implant end 351 is passed through aperture 355 of anchor 353 and is drawn back along a tissue insertion path to achieve desired positioning and tensioning of implant 350 relative to urethra 360. When the desired amount of tension is achieved on implant 350, or supportive force on urethra 360, end 351 of implant 350, drawn through aperture 355, may be fastened or otherwise coupled or locked by a clip, or by any other means, to implant 350, to secure the position of implant 350.

Figure 20B:
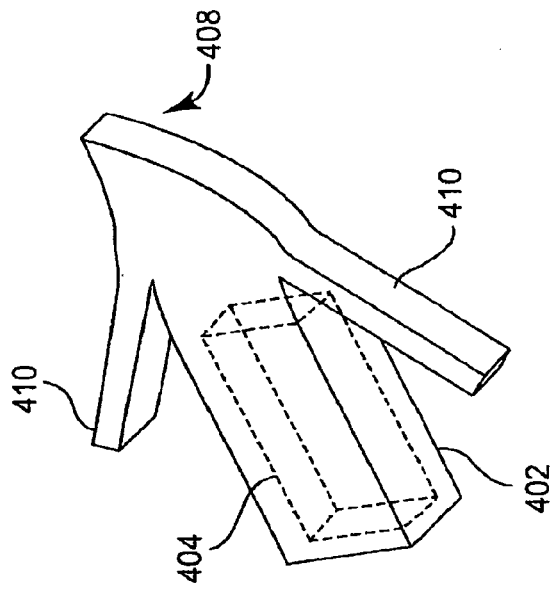
FIGS. 20A, 20B, 20C, and 20D illustrate an embodiment of a self-fixating tip according to the invention.
Figure 20D:
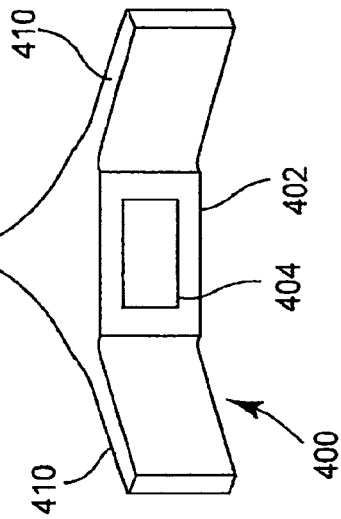
Figure 20A:
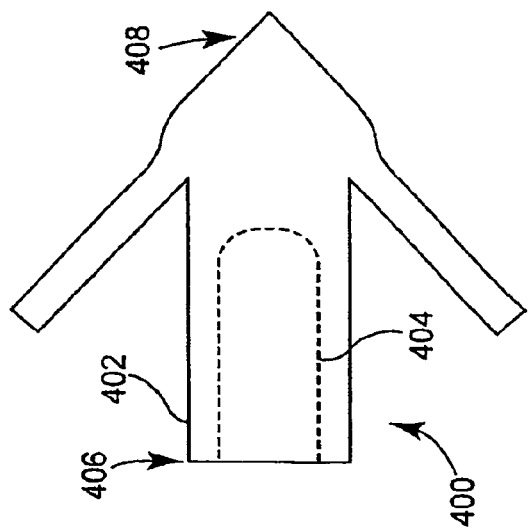
Figure 20C:
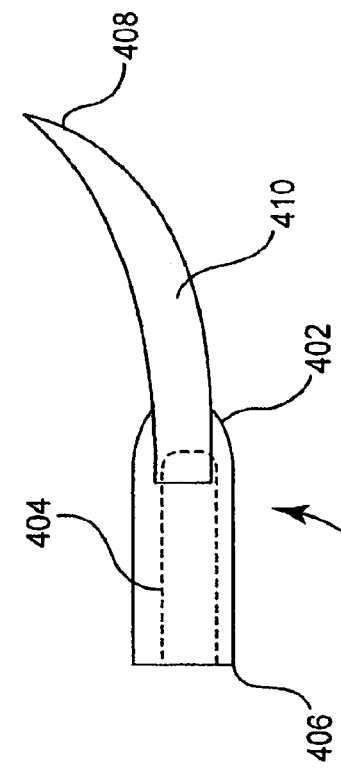

Another example of a useful self-fixating tip according to the present description, is illustrated at FIGS. 20A through 20D. Self-fixating tip 400 includes base 402, proximal base end 406, distal base end 408, and internal channel 404. Extending from base 402 are lateral extensions 410, which extend laterally and in a direction that includes a component toward proximal base end 406. Lateral extensions 410 can be sufficiently rigid to be fixed, to not deflect upon insertion through tissue, or may be capable of deflecting in a proximal direction if desired. Lateral extensions 410 are shown to exhibit a thickness that slightly less than a thickness of base 402 (i.e., a thickness at proximal base end 406), but the thickness of lateral extensions 410 could also be the same as the thickness of based 402. As shown at FIGS. 20C and 20D, distal base end 408 includes a curve.

Figure 21A:
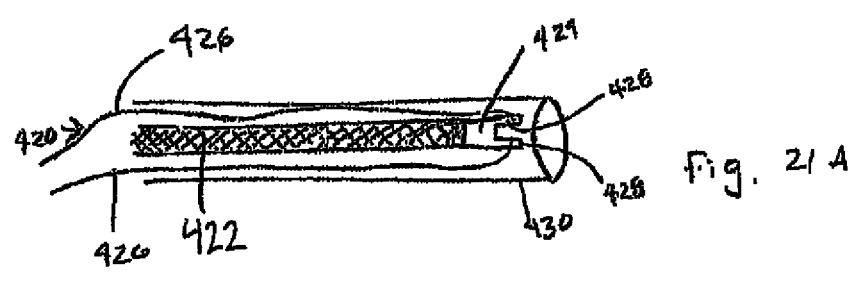
FIGS. 21A and 21B illustrate an embodiment of a portion of an implant according to the invention.
Figure 21B:
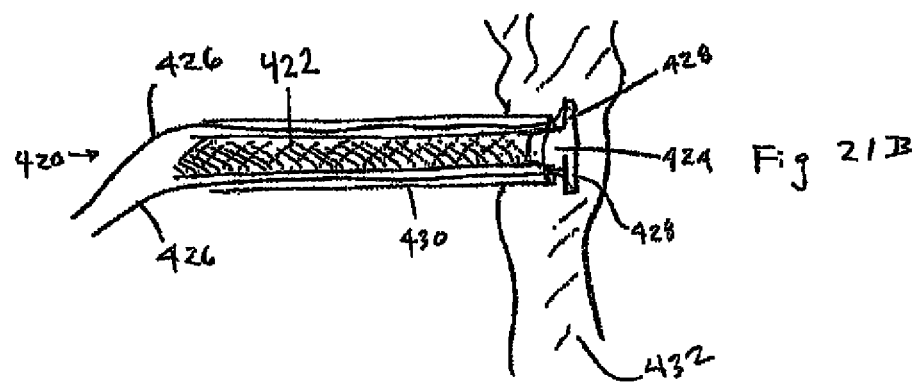

An alternate embodiment of an implant portion is illustrated at FIGS. 21A and 21B. Implant portion 420 includes mesh 422 and self-fixating tip 424 (including one or more features as described herein), contained by hollow elongate inserter 430. Self-fixating tip 424 includes moveable section 428, and two optional sutures 426, one attached to each moveable section 428. During use, self-fixating tip 424 can be inserted into pelvic tissue 432, as shown at FIG. 21B. Inserter 430 can be withdrawn. Optionally, moveable sections 428 can be biased to extend away from each other, optionally away from a base of self-fixating tip 424, upon removal of inserter 430. Alternately, or in addition, optional sutures 426 can be pulled to cause moveable sections 428 to move laterally and away from each other, optionally away from a base of self-fixating tip 424, to extend into tissue 432 and secure self-fixating tip within tissue 432.

Figure 22:
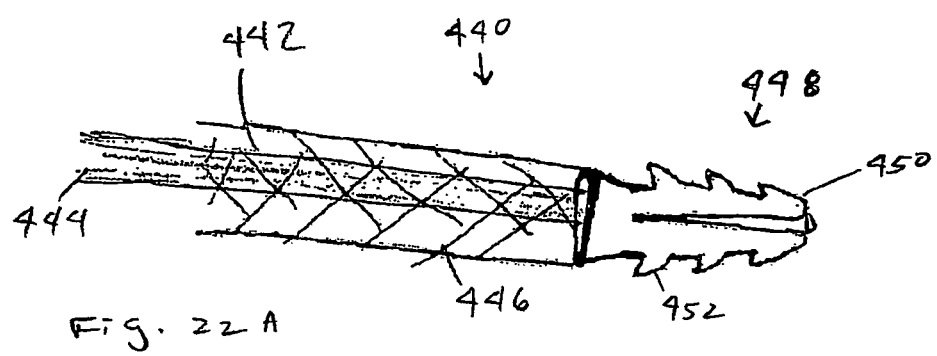
FIGS. 22A and 22B illustrate an embodiment of a portion of an implant according to the invention.
Figure 22:
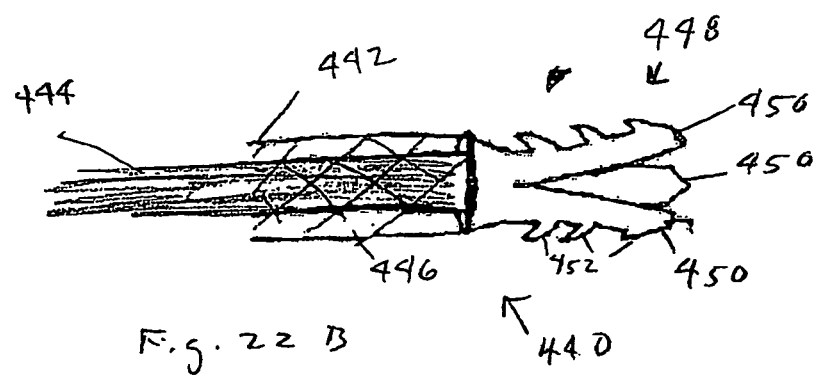

Another alternate embodiment of an implant portion is illustrated at FIGS. 22A and 22B. Implant portion 400 includes mesh 442 and self-fixating tip 448 (including one or more features as described herein). Inserter tool 444 is shown in a position engaging self-fixating tip 448. Self-fixating tip 448 includes three moveable sections 450, each section including three lateral extensions 452. During use, self-fixating tip 448 can be inserted into pelvic tissue and moveable sections 450 can be expanded to increase the size of self-fixating tip 448 within the tissue. Optionally, moveable sections 450 can be biased to extend away from each other, e.g., upon removal of an inserter (not shown). Alternately, or in addition, moveable sections 450 can be cause to extend laterally away from each other, as desired, such a by use of a push-rod or other mechanism (not shown) contained by inserter tool 444, that can be actuated from a proximal end of the inserter tool.

Figure 23A:
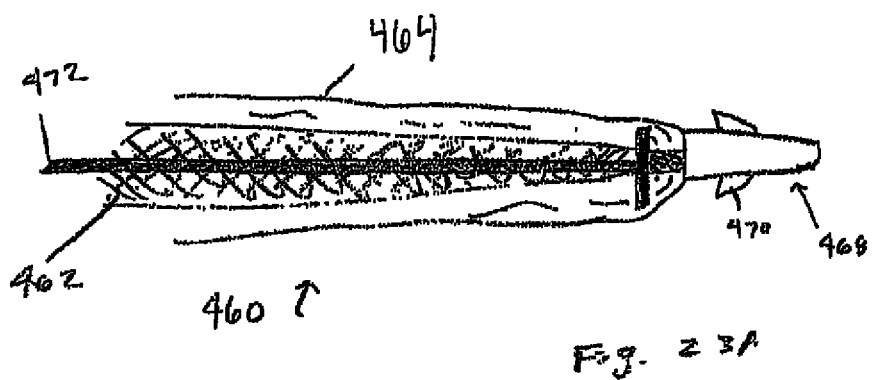
FIGS. 23A and 23B illustrate an embodiment of a portion of an implant according to the invention.
Figure 23B:
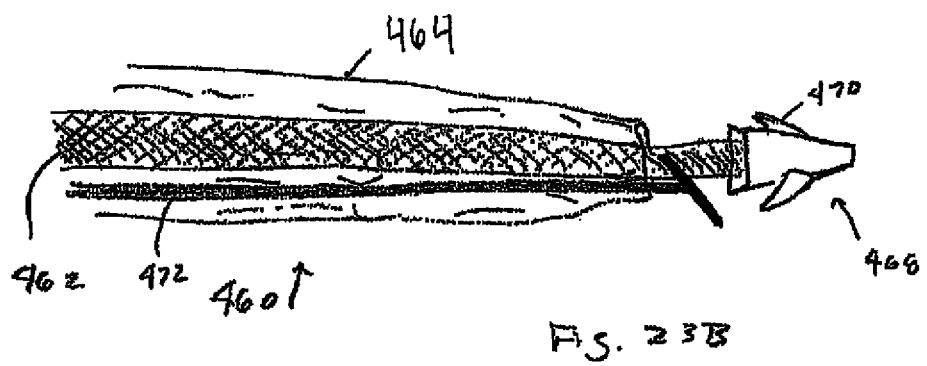

Another alternate embodiment of an implant portion is illustrated at FIGS. 23A and 23B. Implant portion 460 includes mesh 462, plastic protective sheath 464, and self-fixating tip 468 (including one or more features as described herein, including lateral extensions 470). Tool 472 is shown in a position that places a "T" end at a location near self-fixating tip 468; an opposite end of tool 472 is located at a position that is accessible to a physician during an implantation procedure. During use, self-fixating tip 468 can be inserted into pelvic tissue as described herein. Tool 472 can be twisted, turned, or moved, or removed from the location with "T" near self-fixating tip 468, and such movement will cause sheath 464 to tear, break, or otherwise separate, at a location near self-fixating tip 468, so that sheath 464 can be removed.

Although embodiments of the present invention have been described with reference to the treatment of female urinary continence, it should be appreciated that many of these embodiments would also be suitable to repair a variety of pelvic conditions in both males and females. For example, embodiments of the present invention would be suitable for a variety of pelvic floor repairs and/or treatments, including pelvic organ prolapse repair, levator hiatus repair, fecal incontinence treatment, perineal body support and hysterectomy support.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

The invention claimed is:

1. A pelvic implant assembly comprising
a support portion and an extension portion,
a self-fixating tip connected to the extension portion, the self-fixating tip comprising
a base comprising a proximal base end, a distal base end, and a length extending between the proximal base end and the distal base end, the proximal base end being connected to the extension portion,
the base comprising an internal channel extending from the proximal base end at least partially along a length of the base toward the distal base end,
a fixed lateral extension extending from the base, the fixed lateral extension comprising a solid extension body fixed to the base along the length of the base, the solid extension body supporting the lateral extension to prevent the lateral extension from deflecting or moving relative to the base during and after implantation into soft tissue, wherein the solid extension body comprises boundaries that include a leading edge on a distal side of the solid extension body, and a trailing edge on a proximal side of the solid extension body, wherein the trailing edge has a thickness greater than a thickness at the leading edge.

2. The pelvic implant assembly of claim 1 wherein the self-fixating tip has a length measured from the proximal base end to the distal base end, in the range from 0.4 to 1.0 centimeter.

3. The pelvic implant assembly of claim 1 wherein the self-fixating tip includes two or more lateral extensions, all lateral extensions extending in a different direction from locations that are at a same length-wise position of the base.

4. The pelvic implant assembly of claim 1 wherein the leading edge extends away from the base and proximally to meet a trailing edge at a pointed lateral extension tip.

5. The pelvic implant assembly of claim 4 wherein the trailing edge includes a portion having a thickness in the range from 0.2 to 1.5 millimeters.

6. In combination, the pelvic implant assembly of claim 1 and an insertion tool, the insertion tool comprising a handle and a needle extending from the handle, the needle comprising a proximal end attached to the handle and a distal end, the distal end comprising a tip that is adapted to engage the self-fixating tip and to pass the self-fixating tip through tissue by pushing the self-fixating tip.

7. The pelvic implant assembly of claim 1, wherein the implant assembly is a urethral sling comprising a mesh strip and two self-fixating tips, one self-fixating tip fixed at each end of the mesh strip.

8. The pelvic implant assembly of claim 7 wherein the sling has a length in the range from 6 to 10 centimeters.

9. The pelvic implant assembly of claim 1, wherein the self-fixating tip is fixedly attached to the extension portion.

10. The pelvic implant assembly of claim 1 comprising two implant pieces, each implant piece comprising a distal end and a connecting end, each distal end comprising the extension portion, and each connecting end comprising the support portion.

11. The pelvic implant assembly of claim 10 wherein the self-fixating tip is fixedly secured to the distal end of each implant piece.

12. The pelvic implant assembly of claim 1 wherein the lateral extension has a length in the range from 0.5 to 5 millimeters.

13. The pelvic implant assembly of claim 1 wherein the solid extension body includes dimensions of length along the length of the base, width in a direction laterally away from a longitudinal axis of the base, and thickness perpendicular to the length and the width, wherein a width of the solid body is greater than a thickness of the solid body.

14. A method of treating a pelvic condition, the method comprising
providing an implant comprising
a support portion and an extension portion,
a self-fixating tip connected to the extension portion, the self-fixating tip comprising
a base comprising a proximal base end, a distal base end, and a length extending between the proximal base end and the distal base end, the proximal base end being connected to the extension portion,
the base comprising an internal channel extending from the proximal base end at least partially along a length of the base toward the distal base end,
a fixed lateral extension extending from the base, the fixed lateral extension comprising a solid extension body fixed to the base along the length of the base, the solid extension body supporting the lateral extension to prevent the lateral extension from deflecting or moving relative to the base during and after implantation into soft tissue, wherein the solid extension body comprises boundaries that include a leading edge on a distal side of the solid extension body, and a trailing edge on a proximal side of the solid extension body, wherein the trailing edge has a thickness greater than a thickness at the leading edge, providing an insertion tool comprising a handle and a needle extending from the handle, the needle comprising a proximal end attached to the handle and a distal end, the distal end comprising a needle distal end that removably engages the self-fixating tip, engaging the needle distal end with the self-fixating tip, inserting the needle distal end and self-fixating tip through a perineal or vaginal incision in a patient, and inserting the self-fixating tip into tissue in the pelvic region.

15. The method of claim 14 wherein
the pelvic condition is selected from the group consisting of female urinary incontinence, male urinary incontinence, and anterior vaginal prolapse, and
the tissue is obturator internus muscle.

16. The method of claim 14 wherein the self-fixating tip includes two or more fixed lateral extensions, all lateral extensions extending in a different direction from locations that are at a same length-wise position of the base.

17. The method of claim 14, wherein the implant comprises a first implant piece comprising the support portion, the extension portion, and the self-fixating tip, the implant comprising a second implant piece comprising a second support portion, a second extension portion, and a second self-fixating tip, the method comprising:

placing the first implant piece on a first side of a patient with the self-fixating tip engaged at tissue of a first obturator foramen and the support portion below a urethra, and placing the second implant piece on a second side of the patient with the second self-fixating tip engaged at tissue of a second obturator foramen and the second support portion below the urethra.

18. The method of claim 17 comprising attaching the support portion to the second support portion below the urethra.

19. A method of treating a pelvic condition in a patient, the method comprising:

creating a single incision through the vagina or perineal floor;

dissecting tissue near a tissue to be supported;

providing a pelvic implant comprising
a support portion and an extension portion,
a self-fixating tip connected to the extension portion, the self-fixating tip comprising
a base comprising a proximal base end, a distal base end, and a length extending between the proximal base end and the distal base end, the proximal base end being connected to the extension portion,
the base comprising an internal channel extending from the proximal base end at least partially along a length of the base toward the distal base end, and
a fixed lateral extension extending from the base, the fixed lateral extension comprising a solid extension body fixed to the base along the length of the base, the solid extension body supporting the lateral extension to prevent the lateral extension from deflecting or moving relative to the base during and after implantation into soft tissue, wherein the solid extension body comprises boundaries that include a leading edge on a distal side of the solid extension body, and a trailing edge on a proximal side of the solid extension body, wherein the trailing edge has a thickness greater than a thickness at the leading edge, passing the pelvic implant through the incision, implanting the self-fixating tip at tissue of the pelvic region.

20. The method of claim 19 comprising:

dissecting tissue beneath the tissue to be supported;

implanting the self-fixating tip at the obturator foramen on one side of the patient;

implanting a second self-fixating tip at the obturator foramen on a second side of the patient, whereby the implant is suspended between the two obturator foramen;

positioning a portion of the implant below the urethra to support the urethra.

21. The method of claim 20 comprising positioning the first and second self-fixating tips in the obturator internus muscle without puncturing the obturator membrane.

22. The method of claim 20 wherein implanting the self-fixating tip at the obturator foramen comprises engaging the self-fixating tip with an end of an insertion tool and pushing the self-fixating tip into tissue of the obturator foramen.

23. The method of claim 19 comprising adjusting the implant to provide a desired position and amount of support for the urethra by selecting one or more of: a point of insertion of the self-fixating tip within the obturator foramen, and a depth of insertion of the self-fixating tip within the obturator foramen.

24. The method of claim 19 comprising treating a condition selected from the group consisting of incontinence, enterocele, cystocele, rectocele, and vaginal vault prolapse in a female; and incontinence in a male.

25. The method of claim 19 comprising implanting a self-fixating tip in fibrous tissue selected from the group consisting of: the uterosacral ligament, the coccygeous muscle, the sacrospinous ligament, the iliococcygeous muscle, the obturator internus muscle, and the obturator externus muscle.

26. The method of claim 19 wherein the self-fixating tip includes two or more fixed lateral extensions, all lateral extensions extending in a different direction from locations that are at a same length-wise position of the base.

27. The method of claim 19, wherein the pelvic implant comprising a first implant piece comprising the support portion, the extension portion, and the self-fixating tip, and a second implant piece comprising a second support portion, a second extension portion, and a second self-fixating tip, the method comprising placing the first implant piece on a first side of a patient with the self-fixating tip engaged at tissue of a first obturator foramen and the support portion below a urethra, and placing the second implant piece on a second side of the patient with the second self-fixating tip engaged at tissue of a second obturator foramen and the second support portion below the urethra.

28. The method of claim 27 comprising attaching the support portion to the second support portion below the urethra.

* * * * *